(12) United States Patent
Uozumi et al.

(10) Patent No.: US 7,164,026 B2
(45) Date of Patent: Jan. 16, 2007

(54) POLYMER-CARRYING OPTICALLY ACTIVE BINAPHTHYL TYPE OXAZOLINE COMPOUND

(75) Inventors: Yasuhiro Uozumi, Nagoya (JP); Heiko Hoche, Okazaki (JP); Kenzo Sumi, Ohtu-ku (JP)

(73) Assignee: Takasago International Corporation, Tokyo (JP)

( * ) Notice: Subject to any disclaimer, the term of this patent is extended or adjusted under 35 U.S.C. 154(b) by 454 days.

(21) Appl. No.: 10/704,576

(22) Filed: Nov. 12, 2003

(65) Prior Publication Data

US 2004/0097738 A1    May 20, 2004

(30) Foreign Application Priority Data

Nov. 15, 2002    (JP) .............................. 2002-332398

(51) Int. Cl.
C07F 7/02 (2006.01)
C07D 413/02 (2006.01)

(52) U.S. Cl. ........................................ 548/110; 548/237

(58) Field of Classification Search ................ 548/110, 548/237

See application file for complete search history.

(56) References Cited

FOREIGN PATENT DOCUMENTS

| JP | 10-287663 | 10/1998 |
|---|---|---|
| JP | 10-287691 | 10/1998 |
| JP | 11-147890 | 6/1999 |
| JP | 2002-265481 | 9/2002 |
| WO | WO 98/12202 | 3/1998 |
| WO | WO 02/062809 | 2/2002 |

OTHER PUBLICATIONS

Uozumi et al "Design and Preparation of 3,3'-Disubstituted 2,2'-Bis(oxazolyl)-1,1'-binaphthyls (boxax): New Chiral Bis(oxazoline) Ligands for Catalytic Asymmetric Wacker-Type Cyclization" J. Org. Chem. 1999, 64, 1620-1625.*

Cai, et al., "Efficient synthesis of 6-mono-bromo-1,1'-bi-2-naphthol", Tetrahedron Lett rs, vol. 43 (2002), pp. 4055-4057.

* cited by examiner

Primary Examiner—Kamal A. Saeed
(74) Attorney, Agent, or Firm—Fitzpatrick, Cella, Harper & Scinto

(57) ABSTRACT

A polymer-carrying optically active binaphthyl type oxazoline compound having axial asymmetry, represented by the following general formula (1)

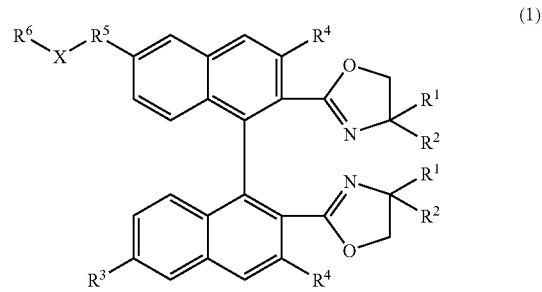

(wherein $R^1$ and $R^2$ may be the same or different from each other and each represents a hydrogen atom, an alkyl group having from 1 to 6 carbon atoms or the like; $R^3$ is a hydrogen atom or —$R^5$—X—$R^6$; $R^4$ is a hydrogen atom or the like; $R^5$ is a straight- or branched-chain aliphatic hydrocarbon chain which may have a directly or indirectly bonded substituent; X is $CH_2$, $CO_2$, O, $CONR^7$ or $NR^7$; $R^6$ is a directly or indirectly bonded polymer; and $R^7$ is a hydrogen atom or the like), and to a transition metal complex which uses the compound as the ligand.

5 Claims, No Drawings

POLYMER-CARRYING OPTICALLY ACTIVE BINAPHTHYL TYPE OXAZOLINE COMPOUND

FIELD OF THE INVENTION

This invention relates to a polymer-carrying optically active binaphthyl type oxazoline compound having axial asymmetry. The polymer-carrying optically active binaphthyl type oxazoline compound having axial asymmetry of the invention is useful as the ligand of catalyst in various asymmetric synthesis reactions which use a transition metal complex catalyst, such as Wacker type asymmetric cyclization reaction of olefin compounds.

BACKGROUND OF THE INVENTION

Many transition metal complexes have been used in the past as the catalysts of organic synthesis reactions, and particularly, noble metal complexes have been broadly used despite of their high prices because they are stable and easy to handle. A large number of studies on syntheses have been conducted using these noble metal complexes and the like transition metal complexes as the catalyst, and a large number of reports have been published which rendered possible organic synthesis reactions including asymmetric reactions that have been considered impossible by the conventional methods.

There are various types of optically active ligands which are used in such asymmetric catalysts, and a 2,2'-bis(oxazolin-2-yl)-1,1'-binaphthyl (to be referred simply to as "boxax" hereinafter in some cases) ligand is one of them that have particularly superior asymmetry recognition. Some cases have been reported in which the Wacker type asymmetric cyclization reaction was carried out using a palladium complex which uses this boxax as the ligand (e.g., References 1 and 2).

However, in spite of the high prices, these catalysts cannot be recovered or can be recovered only by a complex separation method which accompanies many losses, and what is more, recycle of the recovered catalysts is impossible or not economical. Thus, concern has been directed toward the development of a catalyst which can be easily separated and recycled and can effectively retain its activities, particularly selectivity, even after its repeated use.

Synthetic chiral polymers have been broadly studied on their applications to media for the separation of racemic compounds, reagents for asymmetric synthesis, catalysts and the like, and the study on asymmetry recognition among various functions possessed by these chiral polymers is a field which is remarkably progressing in recent years. Particularly, in the application to a stereoselective organic reaction, it can become a reaction which is different from the general homogeneous reaction in terms that a specific system constructed by a polymer is used. When a polymer reagent or a polymer catalyst is used in organic syntheses, there is an advantage in improving industrialization processes from the viewpoints that separation of the formed product becomes easy and recycle of the reagent or catalyst becomes possible.

For example, a transition metal complex having a phosphine ligand containing a polymer-binding type binaphthyl group becomes a heterogeneous catalyst because the polymer is inactive, and it can be said that such a heterogeneous catalyst is advantageous in comparison with a homogeneous catalyst from the viewpoint that it can be easily separation from the reaction mixture.

For example, a phosphine compound having a polymer-bonded binaphthyl group (e.g., References 3 and 4), a phosphine compound having polymer-bonded phosphorus atom and nitrogen atom in the same molecule (e.g., Reference 5), a ruthenium-phosphine complex having a polymer-bonded binaphthyl group (e.g., Reference 6) and the like are known.

Since heterogeneous catalysts can be separated by filtrating the reaction mixture after completion of the reaction, it can be said that they are advantageous from the operation point of view in comparison with homogeneous catalysts, and when these filtered and separated heterogeneous catalysts can be recycled, they also become advantageous from the economical point of view in comparison with homogeneous catalysts. However, it is the present situation that optically active nitrogen-containing ligands which can be recycled are hardly known.

[Reference 1] JP-A-10-287663

[Reference 2] JP-A-10-287691

[Reference 3] JP-T-2000-507604 (The term "JP-T" as used herein means a published Japanese translation of a PCT patent application.)

[Reference 4] JP-A-11-147890

[Reference 5] JP-A-2002-265481

[Reference 6] WO 02/62809

SUMMARY OF THE INVENTION

As described in the foregoing, the invention contemplates providing a polymer-carrying optically active binaphthyl type oxazoline compound which has excellent functions as the catalyst of asymmetric synthesis reactions, for example as the ligand of a heterogeneous catalyst of Wacker type asymmetric cyclization reaction of olefin compounds. Another object of the invention is to provide a synthesis intermediate useful for obtaining a polymer-carrying optically active binaphthyl type oxazoline compound. Still another object of the invention is to provide a method for producing optically active heterocyclic compounds using this polymer-carrying optically active binaphthyl type oxazoline compound.

With the aim of solving the above problems, the present inventors have conducted intensive studies. As a result, an optically active binaphthyl type oxazoline compound having oxazoline at the 2,2'-position of the binaphthyl nucleus and having a group capable of directly or indirectly binding to a polymer at the 6-position was synthesized, and a polymer-carrying optically active binaphthyl type oxazoline compound was obtained by binding the compound to a polymer. The invention has been accomplished by finding that this ligand is excellent as a ligand to be used in asymmetric synthesis reactions.

Accordingly, preferred embodiments of the invention include 1. a polymer-carrying optically active binaphthyl type oxazoline compound having axial asymmetry, represented by the following general formula (1):

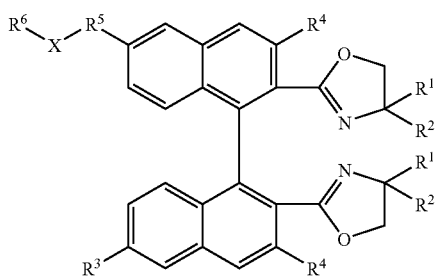

(1)

(wherein $R^1$ and $R^2$ may be the same or different from each other and each represents a hydrogen atom, an alkyl group having from 1 to 6 carbon atoms, an aryl group which may have a substituent or a benzyl group which may have a substituent; $R^3$ represents a hydrogen atom or —$R^5$—X—$R^6$; $R^4$ represents a hydrogen atom, an alkyl group having from 1 to 4 carbon atoms or a tri($C_{1-4}$ alkyl)silyl group; $R^5$ represents a straight- or branched-chain aliphatic hydrocarbon chain which may have a directly or indirectly bonded substituent; X represents $CH_2$, $CO_2$, O, $CONR^7$ or $NR^7$; $R^6$ represents a directly or indirectly bonded polymer; and $R^7$ represents a hydrogen atom or an alkyl group having from 1 to 4 carbon atoms);

2. the oxazoline derivative according to the item 1, wherein the polymer is one or more species selected from polyamides, polystyrenes, polyethers and polyethylenes;

3. a transition metal complex which contains the oxazoline derivative of the item 1 or 2 as the ligand;

4. a transition metal complex which is obtained by allowing a transition metal compound to act upon the oxazoline derivative of the item 1 or 2;

5. the transition metal complex according to the item 3 or 4, wherein the transition metal is at least one transition metal selected from palladium, iridium, rhodium, ruthenium, nickel, copper and platinum;

6. an optically active binaphthyl type oxazoline compound having axial asymmetry, represented by the following general formula (2):

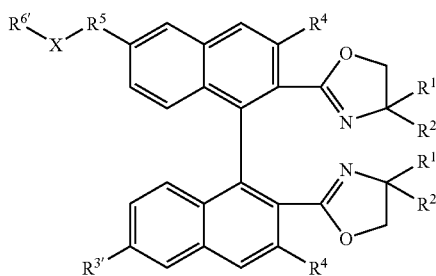

(2)

(wherein $R^1$, $R^2$, $R^4$, $R^5$ and X are as defined in the foregoing; $R^{3'}$ represents a hydrogen atom or —$R^5$—X—$R^{6'}$; and $R^{6'}$ represents a hydrogen atom or an alkyl group having from 1 to 6 carbon atoms);

7. an optically active binaphthyl type amidoalcohol compound having axial asymmetry, represented by the following general formula (3):

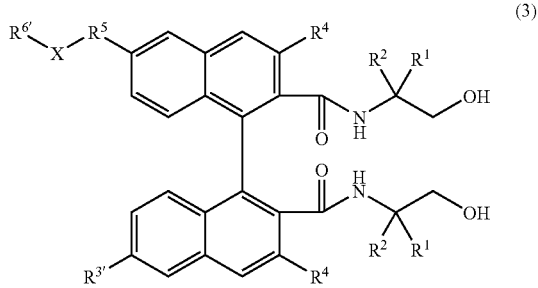

(3)

(wherein $R^1$, $R^2$, $R^{3'}$, $R^4$, $R^5$, $R^{6'}$ and X are as defined in the foregoing);

8. an optically active binaphthyl type carboxylic acid derivative having axial asymmetry, represented by the following general formula (4):

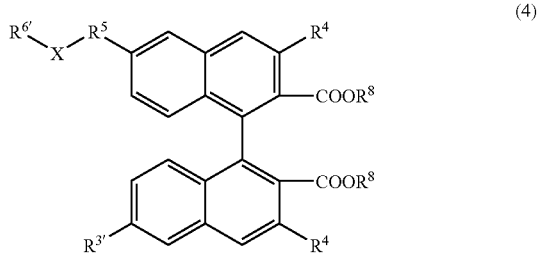

(4)

(wherein $R^{3'}$, $R^4$, $R^5$, $R^{6'}$ and X are as defined in the foregoing; and $R^8$ represents a hydrogen atom or an alkyl group having from 1 to 4 carbon atoms);

9. a method for producing an optically active heterocyclic compound represented by the following general formula (B):

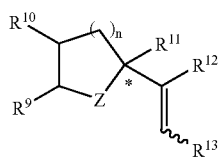

(B)

(wherein Z represents an oxygen atom, a sulfur atom or $NR^{14}$; n is an integer of from 1 to 3; $R^9$, $R^{10}$, $R^{11}$, $R^{13}$ and $R^{14}$ may be the same or different from one another and each represents a hydrogen atom or an alkyl group having from 1 to 4 carbon atoms; $R^{12}$ represents an alkyl group having from 1 to 4 carbon atoms; and $R^{14}$ represents a hydrogen atom or an alkyl group having from 1 to 4 carbon atoms; or $R^9$ and $R^{10}$ may together form a condensed benzene ring)

which comprises oxidizing an olefin compound represented by the following formula (A):

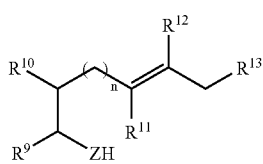

(wherein $R^9$, $R^{10}$, $R^{11}$, $R^{12}$, $R^{13}$, $R^{14}$, Z and n are as defined in the following; and * represents an asymmetric carbon atom) in the presence of the polymer-carrying optically active binaphthyl type oxazoline compound having axial asymmetry described in the item 1 and a divalent palladium salt; and 10. the method for producing optically active heterocyclic compound according to the item 8, wherein Z is oxygen atom.

DETAILED DESCRIPTION OF THE INVENTION

The following describes the invention in detail.

The polymer-carrying optically active binaphthyl type oxazoline compound of the invention having axial asymmetry is a polymer-carrying optically active binaphthyl type oxazoline compound having axial asymmetry, represented by the following general formula (1):

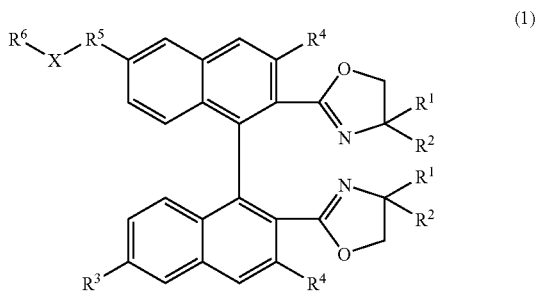

(wherein $R^1$ and $R^2$ may be the same or different from each other and each represents a hydrogen atom, an alkyl group having from 1 to 6 carbon atoms, an aryl group which may have a substituent or a benzyl group which may have a substituent; $R^3$ represents a hydrogen atom or —$R^5$—X—$R^6$; $R^4$ represents a hydrogen atom, an alkyl group having from 1 to 4 carbon atoms or a tri ($C_{1-4}$ alkyl)silyl group; $R^5$ represents a straight- or branched-chain aliphatic hydrocarbon chain which may have a directly or indirectly bonded substituent; X represents $CH_2$, $CO_2$, O, $CONR^7$ or $NR^7$; $R^6$ represents a directly or indirectly bonded polymer; and $R^7$ represents a hydrogen atom or an alkyl group having from 1 to 4 carbon atoms).

When $R^1$ and $R^2$ in the general formula (1) are an alkyl group having from 1 to 6 carbon atoms, its illustrative examples include methyl group, ethyl group, n-propyl group, isopropyl group, n-butyl group, isobutyl group, sec-butyl group, tert-butyl group, pentyl group, hexyl group and the like.

Also, the above alkyl group may have a functional group inert upon asymmetric synthesis reaction as a substituent, preferably within the range of from 1 to 5 groups. Examples of such a substituent include hydroxyl group; methoxy group, ethoxy group, n-propoxy group, isopropoxy group, n-butoxy group, iso-butoxy group, sec-butoxy group, tert-butoxy group and the like alkoxy groups having from 1 to 4 carbon atoms; and fluorine, chlorine, bromine, iodine and the like halogen atoms.

When the $R^1$ and $R^2$ are an aryl group which may have a substituent, its illustrative examples include phenyl group, naphthalen-1-yl group, naphthalen-2-yl group and the like.

Examples of the substituent in case that the $R^1$ and $R^2$ are an aryl group which may have a substituent include an alkyl group having from 1 to 4 carbon atoms, hydroxyl group, an alkoxy group having from 1 to 4 carbon atoms, a halogen atom and the like. These substituents may be contained preferably within the range of from 1 to 5 groups.

Illustrative examples of these substituents include methyl group, ethyl group, n-propyl group, isopropyl group, n-butyl group, isobutyl group, sec-butyl group, tert-butyl group and the like alkyl groups having from 1 to 4 carbon atoms; hydroxyl group; methoxy group, ethoxy group, n-propoxy group, iso-propoxy group, n-butoxy group, iso-butoxy group, sec-butoxy group, tert-butoxy group and the like alkoxy groups having from 1 to 4 carbon atoms; and fluorine, chlorine, bromine, iodine and the like halogen atoms.

Examples of the substituent in case that the $R^1$ and $R^2$ are a benzyl group which may have a substituent include an alkyl group having from 1 to 4 carbon atoms, hydroxyl group, an alkoxy group having from 1 to 4 carbon atoms, a halogen atom and the like. These substituents may be contained preferably within the range of from 1 to 5 groups.

Illustrative examples of these substituents include methyl group, ethyl group, n-propyl group, isopropyl group, n-butyl group, isobutyl group, sec-butyl group, tert-butyl group and the like alkyl groups having from 1 to 4 carbon atoms; hydroxyl group; methoxy group, ethoxy group, n-propoxy group, iso-propoxy group, n-butoxy group, iso-butoxy group, sec-butoxy group, tert-butoxy group and the like alkoxy groups having from 1 to 4 carbon atoms; and fluorine, chlorine, bromine, iodine and the like halogen atoms.

When $R^4$ in the general formula (1) is an alkyl group having from 1 to 4 carbon atoms, its illustrative examples include methyl group, ethyl group, n-propyl group, isopropyl group, n-butyl group, isobutyl group, sec-butyl group, tert-butyl group and the like.

When $R^4$ is a tri($C_{1-4}$ alkyl)silyl group, its illustrative examples include trimethylsilyl group, triethylsilyl group, triisopropylsilyl group, dimethylisopropylsilyl group, dimethyl(2,3-dimethyl-2-butyl)silyl group, tert-butyldimethylsilyl group and the like.

When $R^5$ in the general formula (1) is a straight- or branched-chain aliphatic hydrocarbon chain which may have a substituent, its illustrative examples include methylene group, ethylene group, propylene group, ethylethylene group, trimethylene group, tetramethylene group, pentamethylene group, hexamethylene group and the like alkylene groups having from 1 to 6 carbon atoms; and vinylene group, propenylene group, butenylene group and the like alkenylene groups having from 2 to 4 carbon atoms.

Also, the straight- or branched-chain aliphatic hydrocarbon chain may have a functional group inert upon asymmetric synthesis reaction as a substituent, preferably within the range of from 1 to 5 groups. Examples of such a substituent include methyl group, ethyl group, n-propyl group, isopropyl group, n-butyl group, isobutyl group, sec-butyl group, tert-butyl group and the like alkyl groups having from 1 to 4 carbon atoms; hydroxyl group; methoxy group, ethoxy group, n-propoxy group, iso-propoxy group, n-butoxy group, iso-butoxy group, sec-butoxy group, tert-butoxy group and the like alkoxy groups having from 1 to 4 carbon atoms; and fluorine, chlorine, bromine, iodine and the like halogen atoms.

The directly or indirectly bonded polymer of $R^6$ in the general formula (1) is not particularly limited with the proviso that it is a generally known polymer which is insoluble in solvent at the time of the asymmetric synthesis reaction, and its preferred examples include polyamides, polystyrenes, polyethers, polyethylenes and the like, and its particularly preferred examples include a polystyrene resin so-called Merrifield resin, a polystyrene-divinylbenzene copolymer, a polystyrene-polyethylene glycol resin, a polyamide, an aminomethylated polystyrene resin, a Wong resin, a tender gel resin, an aminomethylated tender gel resin and the like.

It is desirable that this polymer is a polymer directly or indirectly bonded to either one or both of the 6-position and the 6'-position of the binaphthyl group via —$R^5$—X—, preferably a polymer directly bonded to the 6-position alone of the binaphthyl group via —$R^5$—X—, from the view points that a product of interest can be obtained with high optical selectivity and high yield in the asymmetric synthesis reaction and that the performance is hardly reduced when recycled.

When $R^7$ in the general formula (1) is an alkyl group having from 1 to 4 carbon atoms, its illustrative examples include methyl group, ethyl group, n-propyl group, isopropyl group, n-butyl group, isobutyl group, sec-butyl group, tert-butyl group and the like.

As a preferred example of the —$R^5$—X—$R^6$, —$(CH_2)_n$—$CONR^{11}$— Poly (n is an integer of from 1 to 3, $R^{11}$ is hydrogen atom or an alkyl group having from 1 to 4 carbon atoms, and Poly is Merrifield resin) can be cited.

The optically active binaphthyl type oxazoline compound of the invention having axial asymmetry is an optically active binaphthyl type oxazoline compound having axial asymmetry, represented by the following general formula (2):

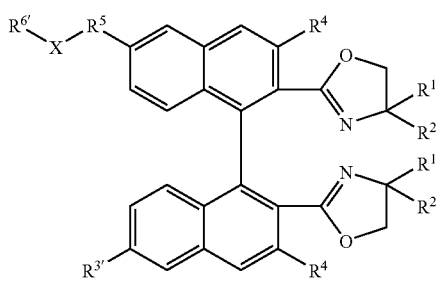

(2)

(wherein $R^1$, $R^2$, $R^4$, $R^5$ and X are as defined in the foregoing; $R^{3'}$ represents a hydrogen atom or —$R^5$—X—$R^{6'}$; and $R^{6'}$ represents a hydrogen atom or an alkyl group having from 1 to 6 carbon atoms).

The optically active binaphthyl type oxazoline compound of the invention having axial asymmetry, represented by the general formula (2), is an intermediate for the production of the polymer-carrying optically active binaphthyl type oxazoline compound having axial asymmetry represented by the general formula (1).

The optically active binaphthyl type oxazoline compound of the invention having axial asymmetry, represented by the general formula (2), can also be used, for example, as a ligand of a homogeneous catalyst for the Wacker type asymmetric cyclization reaction of olefin compounds.

As illustrative examples of the $R^1$, $R^2$, $R^4$, $R^5$ and X in the general formula (2), the same groups described in the foregoing can be cited.

When $R^{6'}$ in the general formula (2) is an alkyl group having from 1 to 6 carbon atoms, its illustrative examples include methyl group, ethyl group, n-propyl group, isopropyl group, n-butyl group, isobutyl group, sec-butyl group, tert-butyl group, pentyl group, hexyl group and the like.

The optically active binaphthyl type amidoalcohol compound of the invention having axial asymmetry is an optically active binaphthyl type amidoalcohol compound having axial asymmetry, represented by the following general formula (3):

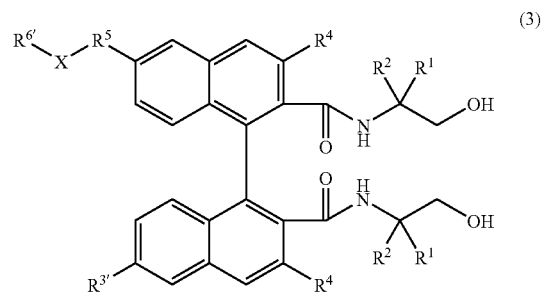

(3)

(wherein $R^1$, $R^2$, $R^{3'}$, $R^4$, $R^5$, $R^{6'}$ and X are as defined in the foregoing).

The optically active binaphthyl type amidoalcohol compound of the invention having axial asymmetry, represented by the general formula (3), is an intermediate for the production of the polymer-carrying optically active binaphthyl type oxazoline compound having axial asymmetry represented by the general formula (1).

As illustrative examples of the $R^1$, $R^2$, $R^3$, $R^4$, $R^5$ $R^{6'}$ and X in the general formula (3), the same groups described in the foregoing can be cited.

The optically active binaphthyl type amidoalcohol compound of the invention having axial asymmetry is an optically active binaphthyl type carboxylic acid derivative having axial asymmetry, represented by the following general formula (4):

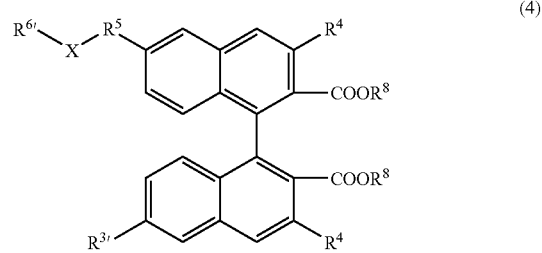

(4)

(wherein $R^{3'}$, $R^4$, $R^5$, $R^{6'}$ and X are as defined in the foregoing; and $R^8$ is hydrogen atom or an alkyl group having from 1 to 4 carbon atoms).

The optically active binaphthyl type oxazoline compound of the invention having axial asymmetry, represented by the general formula (4), is an intermediate for the production of the polymer-carrying optically active binaphthyl type oxazoline compound having axial asymmetry represented by the general formula (1).

As illustrative examples of the $R^{3'}$, $R^4$, $R^5$, $R^{6'}$ and X in the general formula (4), the same groups described in the foregoing can be cited.

When $R^8$ in the general formula (4) is an alkyl group having from 1 to 4 carbon atoms, its illustrative examples include methyl group, ethyl group, n-propyl group, isopropyl group, n-butyl group, isobutyl group, sec-butyl group, tert-butyl group and the like.

Production method of the polymer-carrying optically active binaphthyl type oxazoline compound of the invention represented by the general formula (1) is described in the following.

Firstly, for the purpose of avoiding complications, the production method of the compound of the invention is described with reference to an optically active and (S,S)-form substance of a compound represented by the following formula (I):

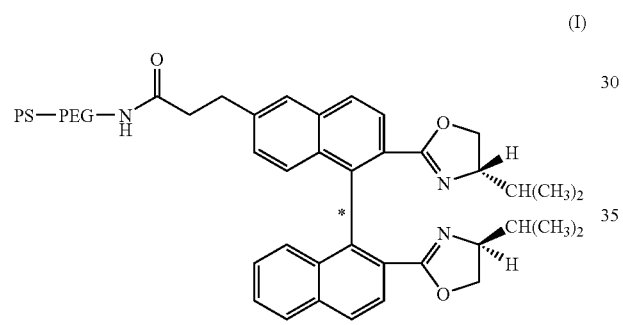

(wherein PS-PEG is a polystyrene-polyethylene glycol resin; and * represents axial asymmetry activity), as an example of the compound of the invention represented by the general formula (1) in which $R^1$ is isopropyl group (—CH(CH$_3$)$_2$), $R^2$, $R^3$ and $R^4$ are hydrogen atoms, $R^5$ is ethylene group (—CH$_2$CH$_2$), X is CONH and $R^6$ is a polystyrene-polyethylene glycol resin (PS-PEG)(polystyrene-polyethylene glycol-(S)-6-(2-methoxycarbonyl)ethyl-2,2'-bis((S)-4-isopropyloxazolin-2-yl)-1,1'-binaphthyl; sometimes to be referred simply to as "PS-PEG-(S,S)-ip-boxax" hereinafter). However, the invention is not limited to this example. In this connection, in the following general formulae, the compound represented by formula (X) is one of the general formula (2) of the invention; the compound represented by formula (IX) is one of the general formula (3) of the invention; and the compound represented by formula (VIII) is one of the general formula (4) of the invention.

The compound (I) described in the above is produced, for example, by the method shown by the following reaction schemes (1) to (5). In these reaction schemes, * represents axial asymmetry activity, Me is methyl group, Piv is pivaloyl group, Bu is butyl group, Tf is trifluoromethanesulfonyl group and PS-PEG represents a polystyrene-polyethylene glycol resin.

[Reaction scheme (1)]

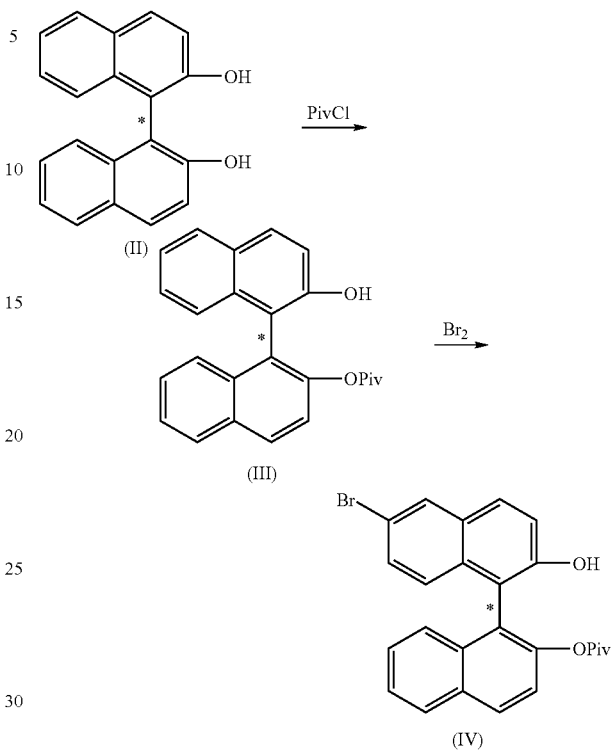

[Reaction scheme (2)]

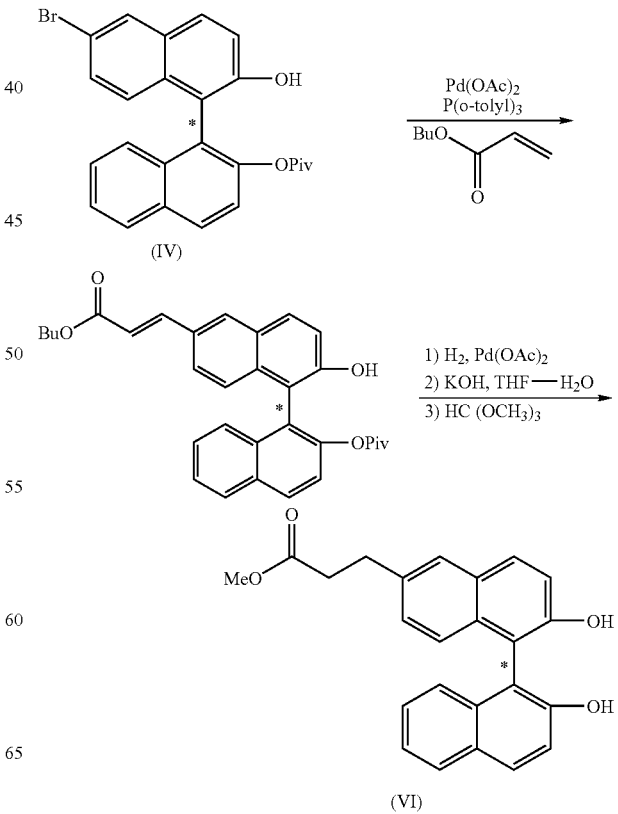

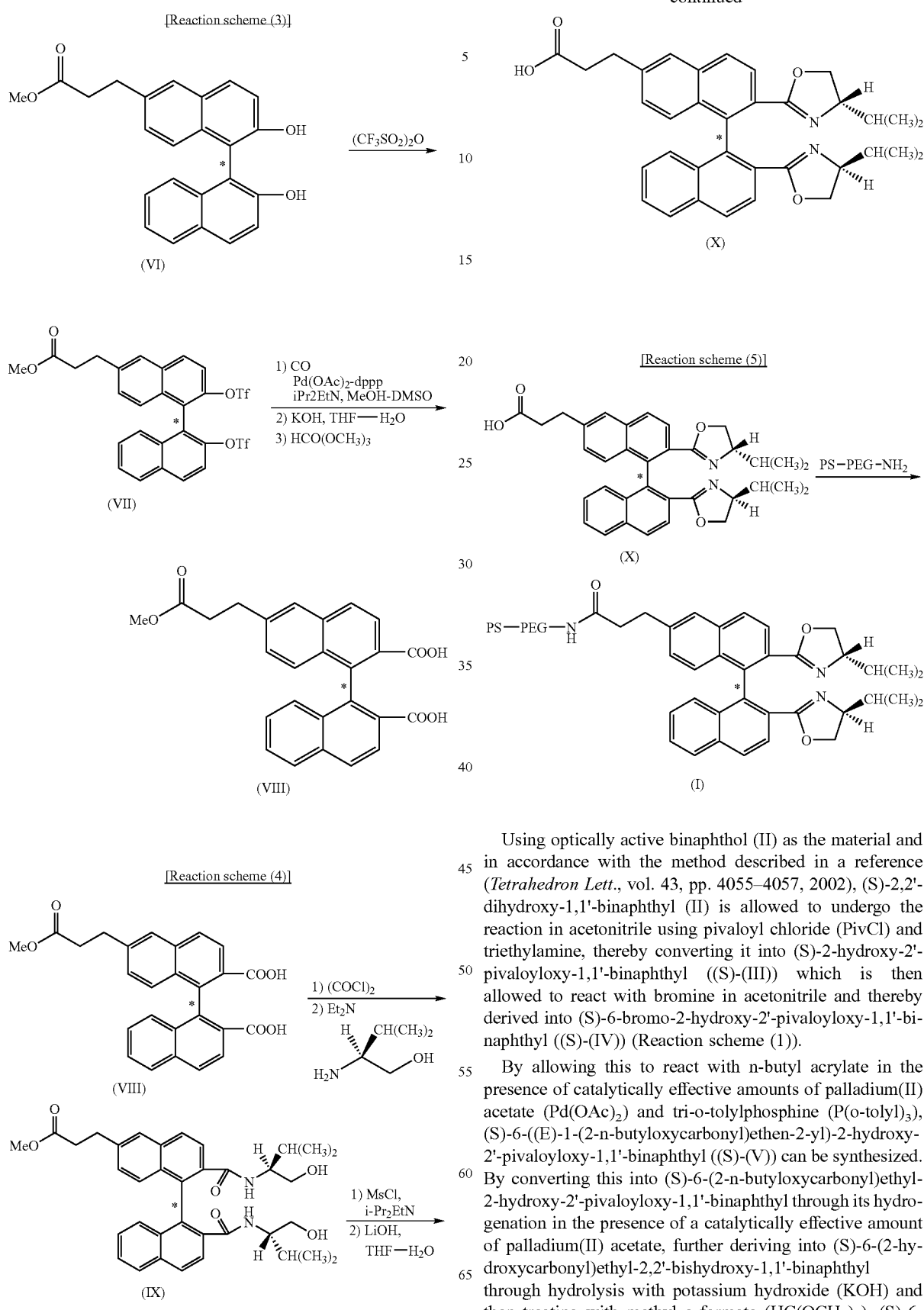

Using optically active binaphthol (II) as the material and in accordance with the method described in a reference (*Tetrahedron Lett.*, vol. 43, pp. 4055–4057, 2002), (S)-2,2'-dihydroxy-1,1'-binaphthyl (II) is allowed to undergo the reaction in acetonitrile using pivaloyl chloride (PivCl) and triethylamine, thereby converting it into (S)-2-hydroxy-2'-pivaloyloxy-1,1'-binaphthyl ((S)-(III)) which is then allowed to react with bromine in acetonitrile and thereby derived into (S)-6-bromo-2-hydroxy-2'-pivaloyloxy-1,1'-binaphthyl ((S)-(IV)) (Reaction scheme (1)).

By allowing this to react with n-butyl acrylate in the presence of catalytically effective amounts of palladium(II) acetate (Pd(OAc)$_2$) and tri-o-tolylphosphine (P(o-tolyl)$_3$), (S)-6-((E)-1-(2-n-butyloxycarbonyl)ethen-2-yl)-2-hydroxy-2'-pivaloyloxy-1,1'-binaphthyl ((S)-(V)) can be synthesized. By converting this into (S)-6-(2-n-butyloxycarbonyl)ethyl-2-hydroxy-2'-pivaloyloxy-1,1'-binaphthyl through its hydrogenation in the presence of a catalytically effective amount of palladium(II) acetate, further deriving into (S)-6-(2-hydroxycarbonyl)ethyl-2,2'-bishydroxy-1,1'-binaphthyl through hydrolysis with potassium hydroxide (KOH) and then treating with methyl o-formate (HC(OCH$_3$)$_3$), (S)-6-

(2-methoxycarbonyl)ethyl-2,2'-bishydroxy-1,1'-binaphthyl ((S)-(VI)) can be synthesized (Reaction scheme (2)).

Next, by converting this into (S)-6-(2-methoxycarbonyl)ethyl-2,2'-bis(trifluoromethanesulfonyloxy)-1,1'-binaphthyl ((S)-(VII)) by allowing it to undergo the reaction in methylene chloride using trifluoromethanesulfonic acid anhydride (($CF_3SO_2$)$_2$O) and pyridine, further converting into (S)-6-(2-methoxycarbonyl)ethyl-2,2'-bis(methoxycarbonyl)-1,1'-binaphthyl by allowing this to react with carbon monoxide using diisopropylethylamine in methanol-dimethyl sulfoxide (DMSO) in the presence of catalytically effective amounts of palladium(II) acetate and 1,3-bis(diphenylphosphino)propane (dppp), subsequently deriving into (S)-6-(2-hydroxycarbonyl)ethyl-2,2'-bis(hydroxycarbonyl)-1,1'-binaphthyl through its hydrolysis with potassium hydroxide and then treating with methyl o-formate, (S)-6-(2-methoxycarbonyl)ethyl-2,2'-bis(hydroxycarbonyl)-1,1'-binaphthyl ((S)-(VIII)) can be synthesized (Reaction scheme (3)).

By converting this into an acid chloride through its treatment with oxalyl chloride and then allowing to react with (S)-valinol, (S)-6-(2-hydroxycarbonyl)ethyl-2,2'-diamido-(N,N'-bis((S)-1-amino-1-isopropyl-2-hydroxyethane)-1,1'-binaphthyl ((S)-(IX)) is obtained. By converting this amide into (S)-6-(2-methoxycarbonyl)ethyl-2,2'-bis((S)-4-isopropyloxazolin-2-yl)-1,1'-binaphthyl through its reaction in methylene chloride using methanesulfonyl chloride (MsCl) and diisopropylethylamine, and then carrying out its hydrolysis with lithium hydroxide, (S)-6-(2-hydroxycarbonyl)ethyl-2,2'-bis((S)-isopropyloxazolin-2-yl)-1,1'-binaphthyl ((S,S)-(X)) can be synthesized (Reaction scheme (4)).

By allowing this to react with an amino group-containing polymer unit (PS-PEG-NH$_2$) (ArgoGel Amine Resin: mfd. by Argonaut Technologies Inc.) in the presence of 1-(3-dimethylaminopropyl)-3-ethylcarbodiimide (EDCl) and N-hydroxybenzotriazole (HOBt), polystyrene-polyethylene glycol-(S)-6-(2-methoxycarbonyl)ethyl-2,2'-bis((S)-4-isopropyloxazolin-2-yl)-1,1'-binaphthyl (PS-PEG-(S,S)-ipboxax) (((S,S)-(I)) can be synthesized (Reaction scheme (5)).

The sequence of reaction operations of the above method can be optionally changed within such a range that it does not cause a difficulty in carrying out the reactions.

The above method can also be used in the same manner for obtaining a compound represented by the general formula (1) in which $R^1$ is isopropyl group (—CH(CH$_3$)$_2$), $R^2$, $R^3$ and $R^4$ are hydrogen atoms, $R^5$ is ethylene group (—CH$_2$CH$_2$—), X is CONH and $R^6$ is a polystyrene-polyethylene glycol resin (PS-PEG).

For example, in describing preparation method of a compound in which $R^1$ and $R^2$ are other than the formula (I), the compound of interest can be obtained making use of a corresponding 2-aminoalcohol instead of valinol.

Examples of the corresponding 2-aminoalcohol include racemic bodies and optically active substances of glycinol, phenylglycinol, alaninol, phenylalaninol, valinol, leucinol, isoleucinol, tert-leucinol, 2-amino-2-methyl-1-propanol and the like, of which optically active substances are desirably used.

Also, for preparing a compound in which $R^3$ is methyl group, it can be easily effected by using (S)-3,3'-dimethyl-2,2'-dihydroxy-1,1'-binaphthyl instead of the (S)-2,2'-dihydroxy-1,1'-binaphthyl (II) which is the starting material of the above reaction. In describing preparation method of a compound in which $R^3$ is other than hydrogen atom and methyl group, the compound of interest can be obtained by making use of a corresponding 3,3'-di-substituted-2,2'-dihydroxy-1,1'-binaphthyl derivative similar to the case of methyl group.

In addition, in describing a method for preparing a polymer-carrying compound in which $R^6$ is other than the formula (I), the compound of interest can be obtained by making use of a corresponding amino group-containing polymer unit instead of the amino group-containing polymer unit (PS-PEG-NH$_2$) (ArgoGel Amine Resin: mfd. by Argonaut Technologies Inc.).

Examples of the corresponding amino group-containing polymer unit include an amino group-containing polystyrene (PS—NH$_2$) (an aminomethylated polystyrene: mfd. by Novabiochem), a copolymer of acrylamidopropyl[2-aminopropyl]poly(ethylene glycol) with N,N-dimethylacrylamide (PEGA-NH$_2$) (reference: Tetrahedron Lett., vol. 33, p. 3077, 1992), a methoxypoly(ethylene glycol) (MeO-PEG) (mfd. by Fluka) and the like.

The polymer-carrying optically active binaphthyl type oxazoline compound (1) of the invention obtained in this manner forms a transition metal complex as the ligand. Examples of the complex-forming transition metal include palladium, iridium, rhodium, ruthenium, nickel, copper, platinum and the like, and preferred examples of the complex to be formed include transition metal phosphine complexes represented by the following general formula (5).

$$[M_mL_nW_pU_q]_rZ_s \qquad (8)$$

(In this formula, M is a transition metal selected from the group consisting of palladium, iridium, rhodium, ruthenium, nickel, copper and platinum; L is a polymer-carrying optically active binaphthyl type oxazoline compound of the general formula (1); and W, U, m, n, p, q, r and s are, when M is palladium, (i) W is chlorine, bromine or iodine, showing m=n=r=1, p=2 and q=s=0, (ii) W is allyl group, showing m=n=p=r=0 and q=s=0, (iii) Z is BF$_4$, ClO$_4$, OTf, PF$_6$, SbF$_6$ or BPh$_4$, showing m=n=r=1, p=q=0 and s=2, (iv) W is an alkyl nitrile having from 1 to 5 carbon atoms, benzonitrile, phthalonitrile, pyridine, dimethyl sulfoxide, dimethylformamide, dimethylacetamide or acetone, Z is BF$_4$, ClO$_4$, OTf, PF$_6$, SbF$_6$ or BPh$_4$, showing m=n=r=1, p=s=2 and q=0, when M is iridium or rhodium, (i) W is chlorine, bromine or iodine, showing m=n=p=1, r=2 and q=s=0, (ii) W is 1,5-cyclooctadiene or norbornadiene, Z is BF$_4$, ClO$_4$, OTf, PF$_6$, SbF$_6$ or BPh$_4$, showing m=n=p=r=0 and q=s=0, (iii) Z is BF$_4$, ClO$_4$, OTf (Tf is trifurate (SO$_3$CF$_3$), PF$_6$, SbF$_6$ or BPh$_4$ (Ph is phenyl group), showing m=n=p=r=s=1 and q=0, (iii) Z is BF$_4$, ClO$_4$, OTf, PF$_6$, SbF$_6$ or BPh$_4$, showing m=r=s=1, n=2 and q=0, when M is ruthenium, (i) W is chlorine, bromine or iodine, Z is a trialkyl amine, showing m=p=s=1, n=r=2 and q=0, (ii) W is chlorine, bromine or iodine, Z is pyridyl group or ring-substituted pyridyl group, showing m=n=r=s=1, p=2 and q=0, (iii) W is a carboxylate group, showing m=n=r=1, p=2 and q=s=0, (iv) W is chlorine, bromine or iodine, Z is dimethylformamide or dimethylacetamide, showing m=n=r=1, p=2 and q=0 and s showing an integer of from 0 to 4, (v) W is chlorine, bromine or iodine, U is chlorine, bromine or iodine, Z is a dialkyl ammonium ion, showing m=n=p=2, q=3, and r=s=1, (vi) W is chlorine, bromine or iodine, U is an aromatic compound or olefin as a neutral ligand, Z is chlorine, bromine, iodine or 13, showing m=n=p=q=r=s=1, (vii) Z is BF$_4$, ClO$_4$, OTf, PF$_6$, SbF$_6$ or BPh$_4$, showing m=n=r=1, p=q=0 and s=2, (viii) W and U may be the same or different from each other and each is hydrogen atom, chlorine, bromine, iodine, carboxyl group or other anion group, Z is a diamine compound, showing m=n=p=q=r=s=1, when M is nickel, (i) W is chlorine, bromine or iodine, showing m=n=r=1, p=2 and q=s=0, (ii) Z is $BF_4$, $ClO_4$, OTf, $PF_6$, $SbF_6$ or $BPh_4$, showing m=n=r=1, p=q=O and s=2, when M is copper, W is hydrogen atom, fluorine, chlorine, bromine or iodine, showing m=p=4, n=2, r=1 and q=s=0, and when M is platinum, (i) W is an alkyl nitrile having from 1 to 5 carbon atoms, benzonitrile, phthalonitrile, pyridine, dimethyl sulfoxide, dimethylformamide, dimethylacetamide or acetone, Z is $BF_4$, $ClO_4$, OTf, $PF_6$, $SbF_6$ or $BPh_4$, showing m=n=r=1, p=s=2 and q=0, (ii) W is chlorine, bromine or iodine, showing m=n=r=1, p=2 and q=s=0, (iii) W is chlorine, bromine or iodine, U is $SnCl_2$, showing m=n=q=r=1, p=2 and s=0, (iv) W is chlorine, bromine or iodine U is $SnCl_3$, showing m=n=p=q=r=1 and s=0.)

Though production method of the complex (8) of transition metal complexes is not particularly limited, it can be produced for example by the methods shown below or modified methods thereof. In this connection, in the formulae of transition metal complexes shown below, L indicates the compound (1) of the invention, cod indicates 1,5-cyclooctadiene, nbd indicates norbornadiene, Ph indicates phenyl group, Ac indicates acetyl group, acac indicates acetylacetonato, dmf indicates dimethylformamide, en indicates ethylenediamine and DPEN indicates diphenylethylenediamine, respectively.

Palladium complex: Regarding the method for producing a palladium complex, it can be prepared for example by allowing the compound (1) of the invention to react with π-allyl palladium chloride ([(π-allyl)PdCl]$_2$) in accordance with the methods described in references (*J. Am. Chem. Soc.*, vol. 113, p. 9887, 1991; *J. Chem. Soc., Dalton Trans.*, pp. 2246–2249, 1980; *Tetrahedron Letters*, vol. 37, pp. 6351–6354, 1996).

The following can be cited as illustrative examples of the palladium complex.

$PdCl_2$ (L), $PdBr_2$ (L), $PdI_2$(L), $Pd(OAc)_2$ (L), $Pd(OCOCF_3)_2$ (L), [(π-allyl)Pd(L)]Cl, [(π-allyl)Pd(L)]Br, [(π-allyl)Pd(L)]I, [(π-allyl)Pd(L)]OTf, [(π-allyl)Pd (L)]$BF_4$, [(π-allyl) Pd(L)]$ClO_4$, [(π-allyl) Pd (L)]$SbF_6$, [(π-allyl)Pd (L)]$PF_6$, [(π-allyl)Pd(L)]$BPh_4$, [(Pd(L)](OTf)$_2$, [(Pd(L)] $(BF_4)_2$, [(Pd(L)]$(ClO_4)_2$, [(Pd(L)]$(SbF_6)_2$, [(Pd(L)]$(PF_6)_2$, [(Pd(L)]$(BPh_4)_2$, $PhCH_2Pd(L)$ Cl, $PhCH_2Pd(L)$Br, $PhCH_2Pd$ (L) I, PhPdCl (L), PhPdBr (L), PhPdI (L), Pd (L), [Pd(L)(PhCN)$_2$]$(BF_4)_2$ Iridium complex: Regarding the method for producing an iridium complex, it can be prepared for example by allowing the compound (1) of the invention to react with [(1,5-cyclooctadiene)(acetonitrile)iridium]tetrahydroborate ([Ir(cod)(CH$_3$CN)$_2$]$BF_4$) in an organic solvent under stirring, in accordance with the method described in a reference (*J. Organomet. Chem.*, vol. 428, p. 213, 1992).

The following can be cited as illustrative examples of the iridium complex.

[Ir(L)Cl]$_2$, [Ir(L)Br]$_2$, [Ir(L)I]$_2$, [Ir(cod)(L)]OTf, [Ir(cod)(L)]$BF_4$, [Ir(cod)(L)]$ClO_4$, [Ir(cod)(L)]$SbF_6$, [Ir(cod)(L)]$PF_6$, [Ir(cod)(L)]$BPh_4$, [Ir(nbd)(L)]OTf, [Ir(nbd)(L)]$BF_4$, [Ir(nbd)(L)]$ClO_4$, [Ir(nbd)(L)]$SbF_6$, [Ir(nbd)(L)]$PF_6$, [Ir(nbd)(L)]$BPh_4$, [Ir(L)$_2$]OTf, [Ir(L)$_2$]$BF_4$, [Ir(L)$_2$]$ClO_4$, [Ir(L)$_2$]$SbF_6$, [Ir(L)$_2$]$PF_6$, [Ir(L)$_2$]$BPh_4$, IrCl(cod)(CO)(L), IrBr(cod)(CO)(L), IrI(cod)(CO)(L)

Rhodium complex: Regarding the method for producing a rhodium complex, it can be prepared for example by allowing the compound (1) of the invention to react with bis(1,5-cyclooctadiene)rhodium(I) tetrafluoroborate ([Rh(cod) 2]$BF_4$) in accordance with the method described in "Jikken Kagaku Koza (Experimental Chemistry Course), 4th edition", edited by The Chemical Society of Japan, Vol. 18, Organic Metal Complexes, pp. 339–344, 1991 (Maruzen).

The following can be cited as illustrative examples of the rhodium complex.

[Rh(L)Cl]$_2$, [Rh(L)Br]$_2$, [Rh(L)I]$_2$, [Rh(cod)(L)]OTf, [Rh(cod)(L)]$BF_4$, [Rh(cod)(L)]$ClO_4$, [Rh(cod)(L)]$SbF_6$, [Rh(cod)(L)]$PF_6$, [Rh(cod)(L)]$BPh_4$, [Rh(nbd)(L)]OTf, [Rh(nbd)(L)]$BF_4$, [Rh(nbd)(L)]$ClO_4$, [Rh(nbd)(L)]$SbF_6$, [Rh(nbd)(L)]$PF_6$, [Rh(nbd)(L)]$BPh_4$, [Rh(L)$_2$]OTf, [Rh (L)$_2$]$BF_4$, [Rh(L)$_2$]$ClO_4$, [Rh(L)$_2$]$SbF_6$, [Rh(L)$_2$]$PF_6$, [Rh(L)$_2$]$BPh_4$ Ruthenium complex: Regarding the method for producing a ruthenium complex, it can be prepared for example by heating the compound (1) of the invention and [(1,5-cyclooctadiene)dichlororuthenium]([Ru(cod)Cl$_2$]$_n$) under reflux in an organic solvent in the presence of trialkylamine, in accordance with the method described in a reference (*J. Chem. Soc., Chem. Commun.*, p. 922, 1985). It can also be prepared by heating the compound (1) of the invention and bis[dichloro(benzene)ruthenium]([Ru(benzene)Cl$_2$]$_2$) under reflux in an organic solvent in the presence of dialkylamine, in accordance with the method described in JP-A-11-269185. It can also be prepared by heating the compound (1) of the invention and bis[diiodo(p-cymene)ruthenium]([Ru(p-cymene)I$_2$]$_2$) under stirring in an organic solvent, in accordance with the method described in a reference (*J. Chem. Soc., Chem. Commun.*, p. 1208, 1989). In addition, it can be synthesized by allowing $Ru_2Cl_4(L)_2NEt_3$ obtained in accordance with the method described in a reference (*J. Chem. Soc., Chem. Commun.*, p. 922, 1985) and a diamine compound to react with each other in an organic solvent, in accordance with the method described in JP-A-11-189600.

The following can be cited as illustrative examples of the ruthenium complex.

$Ru(OAc)_2(L)$, $Ru(OCOCF_3)_2(L)$, $Ru_2Cl_4(L)_2NEt_3$, [{RuCl(L)}$_2$(μ-Cl)$_3$][Me$_2$NH$_2$], [{RuBr(L)}$_2$(μ-Br)$_3$][Me$_2$NH$_2$], [{RuI(L)}$_2$(μ-I)$_3$][Me$_2$NH$_2$], [{RuCl(L)}$_2$(μ-Cl)$_3$][Et$_2$NH$_2$], [{RuBr(L)}$_2$ (μ-Br)$_3$][Et$_2$NH$_2$], [{RuI(L)}$_2$(μ-I)$_3$][Et$_2$NH$_2$], $RuCl_2(L)$, $RuBr_2(L)$, $RuI_2(L)$, [$RuCl_2(L)$](dmf)$_n$, $RuCl_2(L)$(pyridine)$_2$, $RuBr_2(L)$(pyridine)$_2$, $RuI_2(L)$(pyridine)$_2$, $RuCl_2(L)$(2,2'-dipyridine), $RuBr_2(L)$(2,2'-dipyridine), $RuI_2(L)$(2,2'-dipyridine), [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [RuI(p-cymene)(L)]I$_3$, [Ru(L)](OTf)$_2$, [Ru(L)]$(BF_4)_2$, [Ru(L)]$(ClO_4)_2$, [Ru(L)]$(SbF_6)_2$, [Ru(L)]$(PF_6)_2$, [Ru(L)]$(BPh_4)_2$, [RuCl$_2$(L)](en), [RuBr$_2$(L)](en), [RuI$_2$(L)](en), [RuH$_2$(L)](en), [RuCl$_2$(L)](DPEN), [RuBr$_2$(L)](DPEN), [RuI$_2$(L)](DPEN), [RuH$_2$(L)](DPEN)

Nickel complex: Regarding the method for producing a nickel complex, it can be prepared for example by dissolving the compound (1) of the invention and nickel chloride (NiCl$_2$) in an organic solvent and then heating the solution under stirring, in accordance with the method described in "Jikken Kagaku Koza, 4th edition", edited by The Chemical Society of Japan, Vol. 18, Organic Metal Complexes, p. 376, 1991 (Maruzen) or the method described in a reference (J. Am. Chem. Soc., 113, 9887, 1991).

The following can be cited as illustrative examples of the nickel complex.

NiCl$_2$(L), NiBr$_2$(L), NiI$_2$(L)

Copper complex: Regarding the method for producing a copper complex, it can be prepared for example by dissolving the compound (1) of the invention and copper(I) chloride (CuCl$_2$) in an organic solvent and then heating the solution under stirring, in accordance with the method described in "Jikken Kagaku Koza, 4th edition", edited by The Chemical Society of Japan, Vol. 18, Organic Metal Complexes, pp. 444–445, 1991 (Maruzen).

The following can be cited as illustrative examples of the copper complex.

Cu$_4$F$_4$(L) 2, Cu$_4$Cl$_4$(L) 2, Cu$_4$Br$_4$(L) 2, Cu$_4$I$_4$(L)$_2$, Cu$_4$H$_4$(L)$_2$

Platinum complex: Regarding the method for producing a platinum complex, it can be prepared for example by dissolving the compound (1) of the invention and dibenzonitrile dichloroplatinum (PtCl$_2$(PhCN)$_2$) and heating the solution under stirring, in accordance with the method described in a reference (*Organometallics*, vol. 10, p. 2046, 1991), if necessary by adding a Lewis acid (SnCl$_2$ or the like).

The following can be cited as illustrative examples of the platinum complex.

PtCl$_2$(L), PtBr$_2$(L), PtI$_2$(L), PtCl$_2$(L)(SnCl$_2$), PtCl(L)(SnCl$_3$)

As a more illustrative example, a palladium complex shown in the following reaction scheme (6) can be cited.

[Reaction scheme (6)]

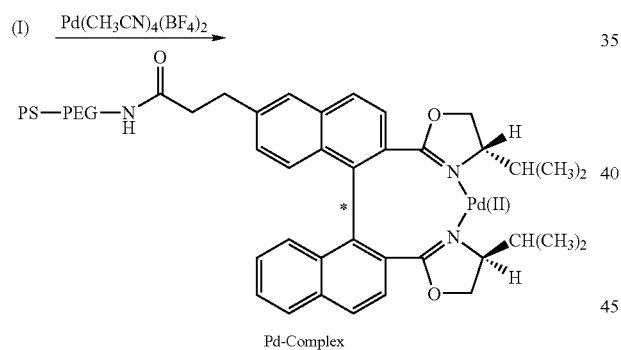

Pd-Complex

The palladium complex obtained by the reaction scheme (6) corresponds to [(Pd(L))](BF$_4$)$_2$.

The polymer-carrying optically active binaphthyl type oxazoline compound (1) of the invention having axial asymmetry can be used, for example, as a catalyst of the method shown below (Wacker type asymmetric cyclization reaction) in which an optically active heterocyclic compound (B) is produced by oxidizing an olefin compound (A) in the presence of a divalent palladium salt.

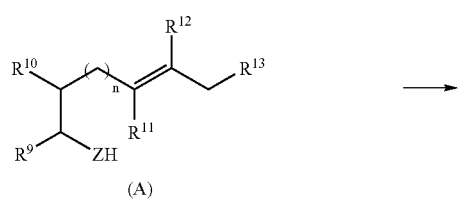

(A)

-continued

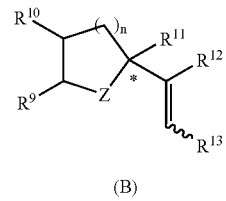

(B)

(In this reaction scheme, Z is oxygen atom, sulfur atom or NR$^{14}$; n is an integer of from 1 to 3; R$^9$, R$^{10}$, R$^{11}$, R$^{13}$ and R$^{14}$ may be the same or different from one another and each represents a hydrogen atom or an alkyl group having from 1 to 4 carbon atoms; R$^{12}$ represents an alkyl group having from 1 to 4 carbon atoms; R$^{14}$ represents a hydrogen atom or an alkyl group having from 1 to 4 carbon atoms; and * represents an asymmetric carbon atom; or R$^9$ and R$^{10}$ may together form a condensed benzene ring.)

That is, in the above reaction, an optically active substance can be synthesized and a product of interest having desired absolute configuration can be obtained by using the polymer-carrying optically active binaphthyl type oxazoline compound (1) and a ligand transition metal complex (illustratively, the palladium complex prepared by the above reaction scheme 6) or using the polymer-carrying optically active binaphthyl type oxazoline compound (1) and a transition metal compound (illustratively, a divalent palladium salt).

When each of R$^9$, R$^{10}$, R$^{11}$, R$^{12}$, R$^{13}$ and R$^{14}$ in the general formulae (A) and (B) is an alkyl group having from 1 to 4 carbon atoms, its illustrative examples include methyl group, ethyl group, n-propyl group, isopropyl group, n-butyl group, isobutyl group, sec-butyl group, tert-butyl group and the like.

Also, when R$^9$ and R$^{10}$ together formed a condensed benzene ring, the formed benzene ring may have a functional group inert upon asymmetric synthesis reaction as a substituent, preferably within the range of from 1 to 5 groups. Examples of such a substituent include methyl group, ethyl group, n-propyl group, isopropyl group, n-butyl group, isobutyl group, sec-butyl group, tert-butyl group and the like alkyl groups having from 1 to 4 carbon atoms; hydroxyl group; methoxy group, ethoxy group, n-propoxy group, iso-propoxy group, n-butoxy group, iso-butoxy group, sec-butoxy group, tert-butoxy group and the like alkoxy groups having from 1 to 4 carbon atoms; and fluorine, chlorine, bromine, iodine and the like halogen atoms.

In the above reaction, using amount of the polymer-carrying optically active binaphthyl type oxazoline compound represented by the general formula (1) varies depending on the reaction vessel and economy, but is within the range of from 0.1 to 50% by mol, preferably from 0.1 to 20% by mol, based on the olefin compound of general formula (A) which is the reaction substrate.

Examples of the divalent palladium salt to be used in the above reaction include palladium chloride, palladium bromide, palladium iodide, palladium acetate, palladium trifluoroacetate, palladium sulfate, palladium nitrate, palladium cyanate, palladium trifluoromethanesulfonate and the like, of which palladium acetate, palladium trifluoroacetate and the like are preferred.

Using amount of the divalent palladium salt is within the range of from 0.1 to 50% by mol, preferably from 0.1 to 20% by mol, based on the olefin compound of general formula (A). Examples of the oxidizing agent include benzoquinone, a combination of copper(II) chloride with oxygen, a combination of copper(II) acetate with oxygen, tert-butyl hydroperoxide, cumin hydroperoxide and the like, of which benzoquinone is preferred.

Using amount of the oxidizing agent is within the range of from 0.01 to 20 equivalents, preferably from 0.1 to 10 equivalents, based on the olefin compound of general formula (A).

The reaction solvent may be any one which is not concerned in the reaction, and its examples include benzene, toluene, xylene and the like aromatic hydrocarbons; pentane, hexane, heptane and the like aliphatic hydrocarbons; cyclohexane, methylcyclohexane and the like alicyclic hydrocarbons; diethyl ether, diisopropyl ether, dioxane, dioxolan, tetrahydrofuran and the like ether solvents; methanol, ethanol, n-propanol, isopropanol, butanol, isobutanol, sec-butanol, tert-butanol, cyclohexanol, benzyl alcohol and the like alcohol solvents; formamide, N,N-dimethylformamide, N,N-dimethylacetamide, N-methylpyrrolidone, hexamethyl phosphate triamide and the like amide solvents; methylene chloride, chloroform, 1,2-dichloroethane, 1,1,2,2-tetrachloroethane, chlorobenzene and the like halogen solvent; and acetone, methyl ethyl ketone, methyl isobutyl ketone, cyclohexanone and the like ketone solvents; as well as acetonitrile, propionitrile, dimethyl sulfoxide and the like solvents, of which methanol, tetrahydrofuran, benzene, methylene chloride and the like are preferred.

These solvents may be used by mixing two or more of them at an optional ratio. Using amount of the solvent is generally from 1 to 1,000 times by volume, preferably from 2 to 500 times by volume, more preferably from 2 to 20 times by volume, based on 1 part by mass of the olefin compound (A).

The reaction temperature is generally from −100° C. to the refluxing temperature of reaction solvent to be used, preferably from −20° C. to 70° C. The reaction time is generally from 0.1 to 100 hours, and these conditions can be optionally changed depending on the amount of reactants and the like to be used.

The cyclization reaction of olefin compound in this oxidation reaction can be carried out by either a batch or a continuous reaction system.

After completion of the reaction, the polymer-carrying optically active binaphthyl type oxazoline compound of the invention represented by the general formula (1) can be separated substantially completely from the reaction mixture by a simple method such as centrifugation or filtration, and the polymer-carrying optically active binaphthyl type oxazoline compound recovered in that case can be recycled as the ligand.

In addition, in the case of a transition metal complex which uses the polymer-carrying optically active binaphthyl type oxazoline compound of the general formula (1) as the ligand, it can be recovered as a transition metal complex when this transition metal complex is a stable complex, and in that case, the recovered transition metal complex can be recycled as the catalyst.

Optical purity of the thus obtained optically active heterocyclic compound can be analyzed by a column chromatography using an optically active column or based on its angle of rotation.

By the use of a member of the polymer-carrying optically active binaphthyl type oxazoline compound represented by the general formula (1) in which axial asymmetry of the binaphthyl nucleus is R-form, the optically active heterocyclic compound can be produced by the above reaction highly selectively. In this case, it is desirable that the 4-position carbon of the oxazoline ring is the optically active asymmetric carbon. In that case, the 4-position asymmetric carbon of the oxazoline ring may be either R-form or S-form. Regarding which of the R-form and S-form of the 4-position asymmetric carbon of the oxazoline ring is to be used, it is desirable to decide it in response to the kind of the reaction substrate olefin compound. That is, a good result may be obtained when the 4-position asymmetric carbon of the oxazoline ring is R-form, or a good result may be obtained when the 4-position asymmetric carbon of the oxazoline ring is S-form, depending on the kind of the olefin compound, so that it is desirable to decide three-dimensional structure of the 4-position asymmetric carbon of the oxazoline ring depending on the reaction substrate.

By the use of a member of the polymer-carrying optically active binaphthyl type oxazoline compound represented by the general formula (1) in which axial asymmetry of the binaphthyl nucleus is S-form, the optically active heterocyclic compound can also be produced by the above reaction highly selectively. In this case, it is desirable that the 4-position carbon of the oxazoline ring is the optically active asymmetric carbon. In that case, the 4-position asymmetric carbon of the oxazoline ring may be either R-form or S-form. Regarding which of the R-form and S-form of the 4-position asymmetric carbon of the oxazoline ring is to be used, it is desirable to decide it in response to the kind of the reaction substrate olefin compound. That is, a good result may be obtained when the 4-position asymmetric carbon of the oxazoline ring is R-form, or a good result may be obtained when the 4-position asymmetric carbon of the oxazoline ring is S-form, depending on the kind of the olefin compound, so that it is desirable to decide three-dimensional structure of the 4-position asymmetric carbon of the oxazoline ring depending on the reaction substrate.

The invention is described below in detail with reference to Examples and Reference Examples, but the invention is not restricted thereby and the invention is not limited to these examples.

SYNTHESIS EXAMPLE 1

Synthesis of (S)-2-hydroxy-2'-pivaloyloxy-1,1'-binaphthyl

A 5.726 g (20.0 mmol) portion of (S)-2,2'-dihydroxy-1,1'-binaphthalene having an optical purity of 99% ee or more and 8.4 ml (60.0 nmol) of triethylamine were dissolved in 60 ml of acetonitrile, and 2.435 g (20.2 mmol) of pivaloyl chloride was added dropwise thereto at 0° C. spending 1 hour. Thereafter, the mixture was stirred at room temperature for 4 hours. After adding 150 ml of diethyl ether to the reaction mixture, the organic layer was washed twice with 30 ml of 1 N hydrochloric acid aqueous solution, twice with 30 ml of saturated NaHCO$_3$ aqueous solution and twice with 30 ml of saturated brine and then dried with magnesium sulfate, subsequently evaporating the solvent. By purifying the resulting residue by a silica gel column chromatography (hexane/ethyl acetate=6/1), 7.16 g of the title compound was obtained as a white solid with a yield of 97%.

Its physical property values are as follows.

$[\alpha]^{25}_D$ −56.8 (C=0.51, THF)

$^1$H-NMR (CDCl$_3$) δ (ppm) 0.78 (s, 9H), 5.13 (s, 1H), 7.06 (d, J=8.4 Hz, 1H), 7.23–7.39 (m, 6H), 7.51 (t, J=5.8 Hz, 1H), 7.82 (d, J=7.6 Hz, 1H), 7.88 (d, J=8.8 Hz, 1H)

$^{13}$C-NMR (CDCl$_3$) δ (ppm) 26.51, 38.79, 114.18, 118.16, 121.74, 122.91, 123.43, 124.49, 125.54, 126.12, 126.56, 127.36, 127.81, 128.23, 128.94, 130.18, 130.62, 132.11, 133.40, 133.53, 148.22, 151.65, 177.67

Anal. calcd for C$_{25}$H$_{22}$O$_3$: C, 81.06; H, 5.99. Found: C, 80.88; H, 6.11.

SYNTHESIS EXAMPLE 2

Synthesis of (S)-6-bromo-2-hydroxy-2'-pivaloyloxy-1,1'-binaphthyl

A 7.10 g (19.2 mmol) portion of (S)-2-hydroxy-2'-pivaloyloxy-1,1'-binaphthyl obtained in Synthesis Example 1 was dissolved in 100 ml of acetonitrile, and 1.96 ml (38.3 mmol) of bromine was slowly added thereto at 0° C. Thereafter, the mixture was stirred at 0° C. for 2 hours and then the reaction was stopped by adding an Na$_2$SO$_3$ aqueous solution. After adding 200 ml of diethyl ether to the reaction mixture, the organic layer was washed with saturated NaHCO$_3$ aqueous solution, 1 N hydrochloric acid aqueous solution and saturated brine and then dried with magnesium sulfate. Thereafter, by evaporating the solvent, 8.86 g of the title compound was obtained as a white solid with a yield of 100%.

Its physical property values are as follows.

$[α]^2_D$ +6.22 (C=0.52, THF)

$^1$H-NMR (CDCl$_3$) δ (ppm) 0.81 (s, 9H), 5.18 (s, 1H), 6.92 (d, J=8.8 Hz, 1H), 7.25–7.40 (m, 5H), 7.51 (td, J$_1$=7.2 Hz, J$_2$=1.2H, 1H), 7.79 (d, J=8.8 Hz, 1H), 7.98 (m, 2H), 8.08 (d, J=8.8 Hz, 1H)

$^{13}$C-NMR (CDCl$_3$) δ (ppm) 26.63, 38.87, 114.42, 117.19, 119.29, 121.68, 122.18, 125.23, 126.18, 126.30, 127.45, 128.26, 129.19, 129.71, 129.75, 129.96, 130.86, 132.04, 133.19, 148.13, 151.95, 177.52

Anal. calcd for C$_{25}$H$_{21}$O$_3$Br: C, 66.83; H, 4.71. Found: C, 66.95; H, 4.88.

SYNTHESIS EXAMPLE 3

Synthesis of (S)-6-bromo-2,2'-dihydroxy-1,1'-binaphthyl

A 6.74 g (15.0 mmol) portion of (S)-6-bromo-2-hydroxy-2'-pivaloyloxy-1,1'-binaphthyl obtained in Synthesis Example 2, 2.52 g (45.0 mmol) of potassium hydroxide, 60 ml of tetrahydrofuran and 20 ml of water were stirred at 25° C. for 14 hours under a stream of nitrogen. After adding 150 ml of ethyl acetate to the reaction mixture, the organic layer was washed five times with 50 ml of 1 N hydrochloric acid aqueous solution and 30 ml of saturated NaHCO$_3$ aqueous solution and twice with 30 ml of saturated brine and then dried with magnesium sulfate. Thereafter, by evaporating the solvent, 5.50 g of the title compound was obtained as a yellow solid with a yield of 100%.

As a result of measurement by a high performance liquid chromatography, its optical purity was found to be 99% ee or more.

Its physical property values are as follows.

$[α]^{25}_D$ +6.3 (C=0.49, THF)

$^1$H-NMR (CDCl$_3$) δ (ppm) 4.99 (s, 1H), 5.08 (s, 1H), 7.02 (d, J=8.0 Hz, 1H), 7.09 (d, J=7.2 Hz, 1H), 7.30–7.41 (m, 5H), 7.51 (t, J=5.8 Hz, 1H), 7.87–7.90 (m, 2H), 7.98 (d, J=8.0 Hz, 1H), 8.04 (s, 1H)

$^{13}$C-NMR (CDCl$_3$) δ (ppm) 110.18, 111.25, 117.78, 117.86, 118.93, 123.99, 124.19, 126.11, 127.66, 128.49, 129.47, 130.36, 130.44, 130.58, 130.69, 131.70, 132.01, 133.27, 152.72, 153.00

Anal. calcd for C$_{20}$H$_{13}$O$_2$Br: C, 65.77; H, 3.59. Found: C, 65.56; H, 3.80.

SYNTHESIS EXAMPLE 4

Synthesis of (S)-6-((E)-1-(hydroxycarbonyl)ethen-2-yl)-2,2'-dihydroxy-1,1'-binaphthyl A 3.60 g (8.0 mmol) portion of (S)-6-bromo-2-hydroxy-2'-pivaloyloxy-1,1'-binaphthyl obtained in Synthesis Example 2, 1.13 g (8.8 mmol) of n-butyl acrylate, 7.40 g (40.0 mmol) of tri-n-butylamine, 122 mg (0.40 mmol) of trio-tolylphosphine, 44 mg (0.20 mmol) of palladium(II) acetate and 20 ml of dimethylformamide were stirred at 130° C. for 36 hours under a stream of nitrogen. After cooling to room temperature and adding 200 ml of diethyl ether, the thus obtained mixed solution was washed twice with 50 ml of 1 N hydrochloric acid aqueous solution, 50 ml of saturated NaHCO$_3$ aqueous solution and saturated brine. The organic layer was dried with magnesium sulfate and then the solvent was evaporated. By purifying the resulting residue by a silica gel column chromatography (hexane/ethyl acetate=5/1), 3.26 g of (S)-6-((E)-1-(n-butyloxycarbonyl)ethen-2-yl)-2-hydroxy-2'-pivaloyloxy-1,1' binaphthyl was obtained as a pale yellow solid with a yield of 82%.

Its physical property values are as follows.

$[α]^{25}_D$ +49.42 (C=0.53, THF)

Anal. calcd for C$_{21}$H$_{14}$O$_4$NBr: C, 59.45; H, 3.33; N, 3.30. Found: C, 59.33; H, 3.40; N, 3.16.

A 400 mg (0.806 mmol) portion of (S)-6-((E)-1-(n-butyloxycarbonyl)ethen-2-yl)-2-hydroxy-2'-pivaloyloxy-1,1'-binaphthyl, 456 mg (8.00 mmol) of potassium hydroxide, 15 ml of tetrahydrofuran and 100 ml of water were stirred at 25° C. for 16 hours. After neutralizing the reaction mixture by adding 15 ml of 1 N hydrochloric acid aqueous solution, this was extracted three times with 30 ml of ethyl acetate. The organic layers were combined and washed with saturated brine, the resulting organic layer was dried with magnesium sulfate, and then the solvent was evaporated. By purifying the resulting residue by a silica gel column chromatography (hexane/ethyl acetate=1/2), 240 mg of the title compound was obtained as a yellow solid with a yield of 84%.

Its physical property values are as follows.

$[α]^{25}_D$ +94.6 (C=0.55, THF)

$^1$H-NMR (DMSO-d$_6$) δ (ppm) 6.47 (d, J=15.9 Hz, 1H), 6.93 (d, J=8.8 Hz, 1H), 6.94 (d, J=7.8 Hz, 1H), 7.18 (td, J$_1$=7.6 Hz, J$_2$=1.2 Hz, 1H), 7.25 (td, J$_1$=7.3 Hz, J$_2$=1.2 Hz, 1H), 7.32 (d, J=9.0 Hz, 1H), 7.36 (d, J=8.8 Hz, 1H), 7.54 (dd, J$_1$=9.0 Hz, J$_2$=1.7 Hz, 1H), 7.69 (d, J=15.9 Hz, 1H), 7.86 (m, 2H), 7.90 (d, J=8.8 Hz, 1H), 8.10 (d, J=1.7 Hz, 1H), 9.26 (s, 1H), 9.51 (s, 1H), 12.27 (s, 1H)

$^{13}$C-NMR (DMSO-d$_6$) δ (ppm) 114.90, 115.92, 117.51, 118.49, 119.13, 122.29, 123.78, 124.21, 125.14, 125.93, 127.79, 127.87, 128.06, 128.36, 128.79, 129.55, 130.18, 133.97, 135.07, 144.31, 152.98, 154.48, 167.74

Anal. calcd for C$_{23}$H$_{16}$O$_4$: C, 77.52; H, 4.53. Found: C, 77.75; H, 4.49.

SYNTHESIS EXAMPLE 5

Synthesis of (S)-6-((E)-1-(n-butyloxycarbonyl)ethen-2-yl)-2,2'-dihydroxy-1,1'-binaphthyl A 7.20 g (19.73 nmol) portion of (S)-6-bromo-2-hydroxy-2'-pivaloyloxy-1,1'-binaphthyl obtained in Synthesis Example 2, 2.82 g (22.0 mmol) of n-butyl acrylate, 18.53 g (100.0 mmol) of tri-n-butylamine, 243 mg (0.80 mmol) of tri-o-tolylphosphine, 89.8 mg (0.40 mmol) of palladium(II) acetate and 100 ml of dimethylformamide were stirred at 130° C. for 36 hours under a stream of nitrogen. After cooling to room temperature and adding 300 ml of ethyl acetate, the thus obtained mixed solution was washed twice with 30 ml of 1 N hydrochloric acid aqueous solution, twice with 30 ml of 5% NaHCO$_3$ aqueous solution, with water and then with saturated brine. The organic layer was dried with magnesium sulfate and then the solvent was evaporated. By purifying the resulting residue by a silica gel column chromatography (hexane/ethyl acetate=2/1), 7.72 g of the title compound was obtained as a yellow oil with a yield of 95%.

Its physical property values are as follows.

$[\alpha]^{25}_D$ +5.38 (C=0.44, THF)

$^1$H-NMR (CDCl$_3$) δ (ppm) 0.88 (t, J=7.4 Hz, 3H), 1.32 (td, J$_1$=7.5 Hz, J$_2$=7.5 Hz, 2H), 1.56 (m, 2H), 2.67 (t, J=7.8 Hz, 2H), 3.06 (t, J=7.8 Hz, 2H), 4.06 (t, J=6.6 Hz, 2H), 5.04 (s, 1H), 5.08 (s, 1H), 7.07 (d, J=8.5 Hz, 1H), 7.14 (d, J=9.0 Hz, 1H), 7.16 (d, J=7.7 Hz, 1H), 7.29 (t, J=7.6 Hz, 1H), 7.34–7.39 (m, 3H), 7.69 (s, 1H), 7.88–7.90 (m, 2H), 7.96 (d, J=9.0 Hz, 1H)

$^{13}$C-NMR (CDCl$_3$) δ (ppm) 13.83, 19.28, 30.82, 64.50, 110.31, 111.63, 117.58, 117.87, 118.49, 123.95, 124.05, 124.96, 125.11, 125.15, 127.52, 128.39, 129.19, 129.38, 130.16, 131.55, 131.86, 133.26, 134.45, 144.21, 152.77, 153.80, 167.08

Anal. calcd for C$_{27}$H$_{24}$O$_4$: C, 78.62; H, 5.86. Found: C, 78.56; H, 5.86.

SYNTHESIS EXAMPLE 6

Synthesis of (S)-3,3'-dimethyl-2-hydroxy-2'-pivaloyloxy-1,1'-binaphthyl

A 4.082 g (13.0 mmol) portion of (S)-3,3'-dimethyl-2,2'-dihydroxy-1,1'-binaphthyl((S)-16) and 5.42 ml (39.0 mmol) of triethylamine were dissolved in 40 ml of acetonitrile, and 1.60 g (13.26 mmol) of pivaloyl chloride was added dropwise thereto at 0° C. spending 1 hour. Thereafter, this was stirred at 25° C. for 4 hours. After adding diethyl ether to the reaction mixture, the organic layer was washed twice with 30 ml of 1 N hydrochloric acid aqueous solution, twice with 30 ml of saturated NaHCO$_3$ aqueous solution and twice with 30 ml of saturated brine and then dried with magnesium sulfate, subsequently evaporating the solvent. By purifying the resulting residue by a silica gel column chromatography (hexane/ethyl acetate=9/1), 3.65 g of the title compound was obtained as a white solid with a yield of 70%.

Its physical property values are as follows.

$[\alpha]^{25}_D$ −76.3 (C=0.55, THF)

$^1$H-NMR (CDCl$_3$) δ (ppm) 0.78 (s, 9H), 2.40 (s, 3H), 2.47 (s, 3H), 5.19 (s, 1H), 6.96 (d, J=8.4 Hz, 1H), 7.27 (t, J=7.4 Hz, 1H), 7.22–7.29 (m, 3H), 7.46 (t, J=7.2 Hz, 1H), 7.70 (s, 1H), 7.73 (d, J=8.4 Hz, 1H), 7.88 (d, J=8.4 Hz, 1H)

$^{13}$C-NMR (CDCl$_3$) δ (ppm) 17.08, 26.51, 38.85, 123.27, 125.40, 125.48, 126.07, 126.37, 126.94, 127.43, 128.90, 129.34, 130.38, 132.26, 147.96

Anal. calcd for C$_{27}$H$_{26}$O$_3$: C, 81.38; H, 6.38. Found: C, 81.27; H, 6.61.

SYNTHESIS EXAMPLE 7

Synthesis of (S)-6-bromo-3,3'-dimethyl-2-hydroxy-2'-pivalyloxy-1,1'-binaphthyl

A 1.99 g (5.0 mmol) portion of (S)-3,3'-dimethyl-2-hydroxy-2'-pivaloyloxy-1,1'-binaphthyl((S)-16) was dissolved in 20 ml of acetonitrile, and 0.51 ml (10.0 mmol) of bromine was slowly added thereto at 0° C. Thereafter, this was stirred at 0° C. for 1 hour and then the reaction was stopped by adding an Na$_2$SO$_3$ aqueous solution. After adding diethyl ether to the reaction mixture, the organic layer was washed with saturated NaHCO$_3$ aqueous solution, 1 N hydrochloric acid aqueous solution and saturated brine and then dried with magnesium sulfate. Thereafter, by evaporating the solvent, 2.36 g of the title compound was obtained as a light yellow solid with a yield of 99%.

Its physical property values are as follows.

$[\alpha]^{25}_D$ −27.1 (C=0.60, THF)

$^1$H-NMR (CDCl$_3$) δ (ppm) 0.80 (s, 9H), 5.28 (s, 1H), 6.84 (d, J=8.8 Hz, 1H), 7.17 (d, J=8.8 Hz, 1H), 7.21–7.31 (m, 3H), 7.47 (td, J$_1$=7.4 Hz, J$_2$=1.2H, 1H), 7.61 (s, 1H), 7.98 (m, 3H)

$^{13}$C-NMR (CDCl$_3$) δ (ppm) 17.03, 17.11, 26.54, 38.88, 117.03, 126.18, 126.52, 127.51, 128.38, 128.66, 128.91, 129.96, 130.65, 132.25, 147.94

Anal. calcd for C$_{27}$H$_{25}$O$_3$Br: C, 67.93; H, 5.28. Found: C, 67.75; H, 4.95.

SYNTHESIS EXAMPLE 8

Synthesis of (S)-6-bromo-3,3'-dimethyl-2,2'-dihydroxy-2'-1,1'-binaphthyl

A 8.0 ml portion of DIBAL-H (1 mol toluene solution: 8.0 mmol) was added to 20 ml diethyl ether solution of (S)-6-bromo-3,3'-dimethyl-2-hydroxy-2'-pivalyloxy-1,1'-binaphthyl obtained in Synthesis Example 7, and then the reaction mixture was stirred overnight at 25° C. A 100 ml portion of diethyl ether was added to the reaction solution, and the reaction was stopped by adding a small amount of water. The organic layer was washed twice with 30 ml of 1 N hydrochloric acid aqueous solution and 30 ml of saturated brine and then dried with magnesium sulfate, subsequently evaporating the solvent. By purifying the resulting residue by a silica gel column chromatography (hexane/ethyl acetate=6/1), 733 mg of the title compound was obtained as a white solid with a yield of 93%.

Its physical property values are as follows.

$[\alpha]^{25}_D$ −20.1 (C=0.55, THF)

$^1$H-NMR (CDCl$_3$) δ (ppm) 2.50 (s, 6H), 5.04 (s, 1H), 5.15 (s, 1H), 6.93 (d, J=9.2 Hz, 1H), 7.02 (d, J=8.4 Hz, 1H), 7.24 (td, J$_1$=7.2 Hz, J$_2$=1.2H, 1H), 7.28 (dd, J$_1$=8.8 Hz, J$_2$=2.0H, 1H), 7.34 (td, J$_1$=6.8 Hz, J$_2$=1.2H, 1H), 7.70 (s, 1H), 7.80 (s, 1H), 7.82 (d, J=6.4 Hz, 1H), 7.96 (d, J=2.0 Hz, 1H)

$^{13}$C-NMR (CDCl$_3$) δ (ppm) 17.02, 17.11, 109.83, 110.78, 117.62, 123.77, 124.00, 125.90, 126.47, 126.97, 127.56, 129.38, 129.45, 129.52, 129.65, 130.49, 130.67, 130.92, 151.95

Anal. calcd for C$_{22}$H$_{17}$O$_2$Br: C, 67.19; H, 4.36. Found: C, 66.97; H, 4.60.

By carrying out syntheses of in and after the following Synthesis Example 9 using the (S)-6-bromo-3,3'-dimethyl-2-hydroxy-2'-pivalyloxy-1,1'-binaphthyl obtained in Synthesis Examples 6 to 8, 3,3'-dimethyl compounds among the compounds of general formulae (1) to (4) of the invention can be synthesized.

SYNTHESIS EXAMPLE 9

Synthesis of (S)-6-(2-methoxycarbonyl)ethyl-2,2'-bishydroxy-1,1'-binaphthyl

A 2.48 g (5.0 mmol) portion of the (S)-6-((E)-1-(n-butyloxycarbonyl) ethen-2-yl)-2-hydroxy-2'-pivaloyloxy-1,1'-binaphthyl obtained as an intermediate in Synthesis Example 4, 5 mg of palladium(II) acetate and 35 ml of ethyl acetate were stirred at 60° C. for 70 hours under a stream of hydrogen. After removing the catalyst by filtration, the solvent was evaporated under a reduced pressure. By purifying the resulting residue by a silica gel column chromatography (hexane/ethyl acetate=5/1), 2.36 g of (S)-6-(1-(2-n-butyloxycarbonyl) ethyl-2-hydroxy-2'-pivaloyloxy-1,1'-binaphthyl as a white foam with a yield of 95%.

Its physical property values are as follows.
$[\alpha]^{25}_D$ −20.71 (C=0.95, THF)
Anal. calcd for $C_{32}H_{34}O_5$: C, 77.08; H, 6.87. Found: C, 76.97; H, 6.71.

A 1.85 g (3.71 mmol) portion of (S)-6-(1-(2-n-butyloxycarbonyl) ethyl-2-hydroxy-2'-pivaloyloxy-1,1'-binaphthyl, 1.06 g (18.60 mmol) of potassium hydroxide, 15 ml of tetrahydrofuran and 100 ml of water were stirred at 25° C. for 16 hours. The reaction mixture was neutralized by adding 50 ml of 1 N hydrochloric acid aqueous solution and then extracted three times with 40 ml of ethyl acetate. The organic layers were combined and washed with saturated brine, the organic layer was dried with magnesium sulfate, and then the solvent was evaporated. By purifying the resulting residue by a silica gel column chromatography (hexane/ethyl acetate=2/1), 1.26 g of (S)-6-(1-(2-hydroxycarbonyl)ethyl-2,2'-bishydroxy-1,1'-binaphthyl was obtained as white glass crystals with a yield of 95%.

Its physical property values are as follows.
$[\alpha]^{25}_D$ +3.05 (C=0.58, THF)
$^1$H-NMR (CDCl$_3$) δ (ppm) 2.72 (t, J=7.8 Hz, 2H), 3.06 (t, J=7.8 Hz, 2H), 5.05 (br s, 2H), 7.08 (d, J=8.8 Hz, 1H), 7.15 (m, 2H), 7.30 (td, $J_1$=6.8 Hz, $J_2$=1.6 Hz, 1H), 7.34–7.39 (m, 3H), 7.69 (d, J=1.2 Hz, 1H), 7.88 (d, J=7.6 Hz, 1H), 7.89 (d, J=8.8 Hz, 1H), 7.96 (d, J=8.8 Hz, 1H)
$^{13}$C-NMR (CDCl$_3$) δ (ppm) 30.41, 35.31, 110.78, 110.83, 117.69, 117.89, 123.96, 124.11, 124.51, 127.02, 127.40, 128.32, 128.36, 129.35, 129.48, 130.89, 131.31, 132.03, 133.30, 135.72, 152.33, 152.59, 177.80
Anal. calcd for $C_{23}H_{18}O_4$: C, 77.08; H, 5.06. Found: C, 77.13; H, 5.10.

A mixed solution composed of 1.26 g (3.52 mmol) of (S)-6-(1-(2-hydroxycarbonyl)ethyl-2,2'-bishydroxy-1,1'-binaphthyl, 5 ml of methyl o-formate, 30 ml of tetrahydrofuran, 5 ml of methanol and 0.3 ml of acetyl chloride was stirred at 25° C. for 24 hours and then concentrated under a reduced pressure. The resulting residue was diluted with 100 ml of ethyl acetate and washed with water, saturated NaHCO$_3$ aqueous solution and saturated brine. The organic layer was dried with magnesium sulfate, and then the solvent was evaporated. By purifying the resulting residue by a silica gel column chromatography (hexane/ethyl acetate=2/1), 1.30 g of the title compound was obtained as white glass crystals with a yield of 99%.

As a result of measurement by a high performance liquid chromatography, its optical purity was found to be 98% ee or more.

Its physical property values are as follows.
$[\alpha]^{24}_D$ +3.67 (C=0.52, THF)
$^1$H-NMR (CDCl$_3$) δ (ppm) 2.68 (t, J=8.0 Hz, 2H), 3.06 (t, J=8.0 Hz, 2H), 3.66 (s, 3H), 5.04 (s, 1H), 5.08 (s, 1H), 7.08 (d, J=8.4 Hz, 1H), 7.15 (m, 2H), 7.30 (td, $J_1$=7.6 Hz, $J_2$=1.2 Hz, 1H), 7.34–7.39 (m, 3H), 7.69 (s, 1H), 7.88 (m, 2H), 7.96 (d, J=9.2 Hz, 1H)
$^{13}$C-NMR (CDCl$_3$) δ (ppm) 30.68, 35.50, 51.62, 110.66, 110.77, 117.60, 117.77, 123.86, 124.04, 124.35, 126.93, 127.30, 128.24, 128.33, 129.26, 129.42, 130.80, 131.21, 131.90, 133.22, 136.00, 152.23, 152.52, 173.09
Anal. calcd for $C_{24}H_{20}O_4$: C, 77.40; H, 5.41. Found: C, 77.61; H, 5.51.

SYNTHESIS EXAMPLE 10

Synthesis of (S)-6-(2-methoxycarbonyl)ethyl-2,2'-bis(trifluoromethanesulfonyloxy)-1,1'-binaphthyl In methylene chloride and at 0° C., 2.17 ml (17.73 mmol) of anhydrous trifluotomethanesulfonic acid was added to a solution of 2.20 g (5.91 mmol) of (S)-6-(2-methoxycarbonyl)ethyl-2,2'-bishydroxy-1,1'-binaphthyl obtained in Synthesis Example 9 and 1 44 ml (17.73 mmol) of pyridine. The reaction mixture was stirred overnight. After adding water to the reaction mixture, the organic layer was washed with 1 N hydrochloric acid aqueous solution. This was dried with magnesium sulfate, and then the solvent was evaporated. By purifying the resulting residue by a silica gel column chromatography (hexane/ethyl acetate=5/1), 3.37 g of the title compound was obtained as a yellow oil with a yield of 90%.

Its physical property values are as follows.
$[\alpha]^{25}_D$ +114.51 (C=0.725, THF)
$^1$H-NMR (CDCl$_3$) δ (ppm) 2.73 (t, J=7.8 Hz, 2H), 3.12 (t, J=7.8 Hz, 2H), 3.67 (s, 3H), 7.17 (d, J=8.8 Hz, 1H), 7.25–7.27 (m, 2H), 7.40 (td, $J_1$=7.6 Hz, $J_2$=1.2 Hz, 1H), 7.56–7.62 (m, 3H), 7.80 (s, 1H), 8.00 (d, J=8.8 Hz, 1H), 8.13 (d, J=9.2 Hz, 1H)
$^{13}$C-NMR (CDCl$_3$) δ (ppm) 30.84, 35.16, 51.74, 116.46, 119.21, 119.42, 119.65, 123.20, 123.39, 126.68, 126.80, 126.88, 127.22, 127.87, 128.24, 129.05, 131.42, 131.73, 131.87, 132.24, 132.46, 133.04, 139.65, 144.95, 145.25, 172.91
Anal. calcd for $C_{26}H_{22}O_8S_2F_6$: C, 48.75; H, 3.46. Found: C, 48.49; H, 3.39.

EXAMPLE 1

Synthesis of (S)-6-(2-methoxycarbonyl)ethyl-2,2'-bis(methoxycarbonyl)-1,1'-binaphthyl (One of the General Formula (4))

An autoclave was charged with 3.32 g (5.22 mmol) of (S)-6-(2-methoxycarbonyl)ethyl-2,2'-bis(trifluoromethanesulfonyl)-1,1'-binaphthyl obtained in Synthesis Example 10, 116 mg (0.52 mmol) of palladium(II) acetate, 214 mg (0.52 mmol) of dppp (1,3-bis(diphenylphosphino)propane), 4.5 ml of diisopropylethylamine, 10 ml of methanol and 30 ml of dimethyl sulfoxide. The mixture was stirred at 120° C. for 72 hours under a carbon monoxide pressure of 0.5 MPa. After cooling, 150 ml of ethyl acetate was added to the reaction mixture. The mixture was washed twice with 50 ml of 1 N hydrochloric acid aqueous solution and then with 30 ml of saturated NaHCO$_3$ aqueous solution and saturated brine. This was dried with magnesium sulfate, and then the solvent was evaporated. By purifying the resulting residue by a silica gel column chromatography (hexane/ethyl acetate=2/1), 1.75 g of the title compound was obtained as a light yellow foam with a yield of 73%.

As a result of measurement by a high performance liquid chromatography, its optical purity was found to be 98% ee or more.

Its physical property values are as follows.

$[\alpha]^{25}_D$ +0.44 (C=0.70, THF)

$^1$H-NMR (CDCl$_3$) δ (ppm) 2.69 (t, J=7.8 Hz, 2H), 3.07 (t, J=7.8 Hz, 2H), 3.48 (s, 3H), 3.50 (s, 3H), 3.67 (s, 3H), 6.98 (d, J=8.8 Hz, 1H), 7.06 (d, J=9.5 Hz, 1H), 7.08 (d, J=7.1 Hz, 1H), 7.23 (td, J$_1$=7.7 Hz, J$_2$=1.2 Hz, 1H), 7.51 (td, J$_1$=7.6 Hz, J$_2$=1.2 Hz, 1H), 7.73 (s, 1H), 7.93 (d, J=8.8 Hz, 2H), 8.00 (d, J=8.8 Hz, 1H), 8.17 (m, 2H)

$^{13}$C-NMR (CDCl$_3$) δ (ppm) 30.84, 35.07, 51.67, 51.80, 51.85, 125.87, 126.17, 126.53, 126.68, 127.07, 127.26, 127.45, 127.51, 127.65, 127.82, 127.93, 131.63, 132.88, 134.82, 135.06, 140.07, 140.18, 140.38, 167.09, 167.10, 173.16

Anal. calcd for C$_{28}$H$_{24}$O$_8$: C, 73.67; H, 5.30. Found: C, 73.60; H, 5.26.

EXAMPLE 2

Synthesis of (S)-6-(2-methoxycarbonyl)ethyl-2,2'-bis(hydroxycarbonyl)-1,1'-binaphthyl (One of the General Formula (4))

The (S)-6-(2-methoxycarbonyl)ethyl-2,2'-bis(methoxycarbonyl)-1,1'-binaphthyl obtained in Example 1 and 618 mg (10.85 mmol) of potassium hydroxide were heated under reflux for 20 hours in a mixed solution of 20 ml of tetrahydrofuran and 10 ml of water. After cooling, the mixed solution was concentrated under a reduced pressure to remove tetrahydrofuran. The concentrated mixture was neutralized by adding 30 ml of 1 N hydrochloric acid aqueous solution and then extracted twice with 50 ml of ethyl acetate. The organic layers were combined and washed with saturated brine, the organic layer was dried with magnesium sulfate and then the solvent was evaporated, thereby obtaining 890 mg of (S)-6-(2-hydroxycarbonyl)ethyl-2,2'-bis(hydroxycarbonyl)-1,1'-binaphthyl (one of the general formula (4)) as a white solid with a yield of 99%.

Its physical property values are as follows.

$[\alpha]^{25}_D$ −1.09 (C=0.52, THF)

$^1$H-NMR (DMSO-d$_6$) δ (ppm) 2.61 (t, J=7.7 Hz, 2H), 2.95 (t, J=7.7 Hz, 2H), 6.79 (d, J=8.8 Hz, 1H), 6.88 (d, J=8.5 Hz, 1H), 7.19 (dd, J$_1$=8.8 Hz, J$_2$=1.7 Hz, 1H), 7.28 (td, J$_1$=7.7 Hz, J$_2$=1.5 Hz, 1H), 7.55 (td, J$_1$=7.6 Hz, J$_2$=1.2 Hz, 1H), 7.85 (d, J=1.0 Hz, 1H), 7.98–8.12 (m, 5H), 12.25 (bs, 3H)

$^{13}$C-NMR (DMSO-d$_6$) δ (ppm) 30.25, 34.57, 126.00, 126.20, 126.62, 126.67, 127.03, 127.36, 127.42, 127.90, 127.91, 128.02, 131.10, 132.47, 134.25, 134.47, 139.33, 139.52, 140.26, 167.59, 167.64, 173.64

Anal. calcd for C$_{25}$H$_{18}$O$_6$: C, 72.46; H, 4.38. Found: C, 72.21; H, 4.38.

A mixed solution composed of 5 ml methanol and 0.3 ml acetyl chloride was added to 890 mg (2.15 mmol) of (S)-6-(2-hydroxycarbonyl)ethyl-2,2'-bis(hydroxycarbonyl)-1,1'-binaphthyl, 3 ml of methyl o-formate and 30 ml of tetrahydrofuran. The resulting mixture was stirred at 25° C. for 24 hours. Thereafter, the solvent was concentrated under a reduced pressure. The resulting residue was diluted with 20 ml of ethyl acetate. The resulting solution was extracted with an NaHCO$_3$ aqueous solution. The thus obtained water layer was neutralized with 1 N hydrochloric acid aqueous solution and then extracted twice with 50 ml of ethyl acetate. The organic layers were combined, washed with saturated brine and then dried with magnesium sulfate. By evaporating the solvent, 870 mg of the title compound was obtained as a white solid with a yield of 94%.

Its physical property values are as follows.

$[\alpha]^{25}_D$ +0.75 (C=0.59, THF)

$^1$H-NMR (CDCl$_3$) δ (ppm) 2.65 (t, J=7.8 Hz, 2H), 3.03 (t, J=7.8 Hz, 2H), 3.64 (s, 3H), 6.80 (d, J=8.8 Hz, 1H), 6.87 (d, J=8.4 Hz, 1H), 6.98 (td, J$_1$=8.8 Hz, J$_2$=1.6 Hz, 1H), 7.47 (td, J$_1$=7.6 Hz, J$_2$=1.2 Hz, 1H), 7.68 (s, 1H), 7.85–7.94 (m, 3H), 8.07 (d, J=8.4 Hz, 1H), 8.09 (d, J=8.4 Hz, 1H), 12.34 (bs, 2H)

$^{13}$C-NMR (CDCl$_3$) δ (ppm) 30.90, 35.08, 51.72, 125.08, 125.48, 126.36, 126.50, 126.64, 127.29, 127.35, 127.54, 127.64, 127.73, 127.77, 127.87, 131.46, 132.70, 135.22, 135.46, 140.31, 141.40, 141.57, 171.82, 173.06

Anal. calcd for C$_{26}$H$_{20}$O$_6$: C, 72.89; H, 4.71. Found: C, 73.00; H, 4.75.

EXAMPLE 3

Synthesis of (S)-6-(2-methoxycarbonyl)ethyl-2,2'-diamido-(N,N'-bis((S)-1-amino-1-isopropyl-2-hydroxy-ethane)-1,1'-binaphthyl((S,S)-ip-amidoalcohol: a Compound of the General Formula (3))

A catalytically effective amount of dimethylformamide was added at 0° C. to a solution prepared by dissolving 1 equivalent of (S)-6-(2-methoxycarbonyl)ethyl-2,2'-bis(hydroxycarbonyl)-1,1'-binaphthyl and 5 equivalents of oxalyl chloride in methylene chloride, and the mixture was then stirred for 5 hours. This reaction mixture was concentrated under a reduced pressure to remove the solvent and excess oxalyl chloride. The thus obtained crude acid chloride was diluted with methylene chloride. At 0° C., to this solution was added a methylene chloride solution containing 2 equivalents of (S)-valinol and 3 equivalents of triethylamine. The reaction mixture was stirred overnight at 25° C. The reaction mixture was diluted with chloroform and washed with 1 N hydrochloric acid aqueous solution, saturated NaHCO$_3$ aqueous solution and saturated brine. The organic layer was dried with magnesium sulfate, and the solvent was evaporated under a reduced pressure. The resulting residue was purified by a silica gel column chromatography (developing solvent: chloroform/methanol or hexane/ethyl acetate). The title compound was obtained as a white solid with a yield of 61%.

Its physical property values are as follows.

$[\alpha]^{25}_D$ −151.34 (C=0.54, THF)

$^1$H-NMR (CDCl$_3$) δ (ppm) 0.50 (d, J=6.4 Hz, 6H), 0.62 (m, 6H), 1.53 (oct, J=6.8 Hz, 2H), 1.84 (s, br, 2H), 2.68 (t, J=7.9 Hz, 2H), 3.07 (t, J=7.9 Hz, 2H), 3.22 (m, 4H), 3.52 (m, 2H), 3.67 (s, 3H), 6.98 (s, br, 1H), 7.08 (s, br, 1H), 7.15–7.21 (m, 3H), 7.32 (td, J$_1$=7.7 Hz, J$_2$=1.6 Hz, 1H), 7.49 (td, J$_1$=7.6 Hz, J$_2$=1.2 Hz, 1H), 7.67 (m, 3H), 7.93 (d, J=8.3 Hz, 1H), 7.95 (d, J=8.3 Hz, 1H), 8.01 (d, J=8.3 Hz, 1H)

$^{13}$C-NMR (CDCl$_3$) δ (ppm) 18.24, 18.30, 19.07, 19.12, 28.72, 30.85, 35.25, 51.70, 57.14, 63.32, 63.46, 123.80, 124.02, 126.57, 126.80, 126.90, 127.17, 127.48, 128.23, 128.62, 128.68, 129.07, 129.07, 131.32, 132.50, 132.67, 122.81, 134.05, 139.56, 170.87, 170.95, 173.17

Anal. calcd for C$_{36}$H$_{42}$O$_6$N$_2$: C, 72.22; H, 7.07; N, 4.68. Found: C, 72.28; H, 7.01; N, 4.59.

EXAMPLE 4

Synthesis of (S)-6-(2-methoxycarbonyl)ethyl-2,2'-diamido-(N,N'-bis((S)-1-amino-1-phenyl-2-hydroxy-ethane)-1,1'-binaphthyl((S,S)-ph-amidoalcohol: a Compound of the General Formula (3))

The same procedure of Example 3 was carried out except that (S)-phenylglycinol was used instead of (S)valinol. The title compound was obtained as a white solid with a yield of 95%.

Its physical property values are as follows.
$[\alpha]^{25}_D$ −133.61 (C=0.51, THF)
$^1$H-NMR (CDCl$_3$) δ (ppm) 2.18 (s, br, 2H), 2.71 (t, J=7.6 Hz, 2H), 3.10 (t, J=7.4 Hz, 2H), 3.41 (m, 4H), 3.63 (s, 3H), 4.81 (m, 2H), 6.72 (m, 2H), 7.08–7.40 (m, 12H), 7.54 (td, J$_1$=7.0 Hz, J$_2$=1.2 Hz, 1H), 7.69 (d, J=8.4 Hz, 1H), 7.71 (d, J=8.8 Hz, 1H), 8.02 (d, J=8.4 Hz, 1H)
$^{13}$C-NMR (CDCl$_3$) δ (ppm) 30.93, 35.25, 51.76, 55.67, 55.71, 65.72, 65.80, 124.06, 124.19, 126.36, 126.45, 126.52, 126.68, 126.76, 126.83, 127.21, 127.27, 127.30, 127.53, 128.27, 128.36, 128.41, 128.66, 128.81, 128.87, 129.09, 131.33, 132.44, 132.57, 132.74, 133.81, 134.03, 134.42, 134.84, 138.20, 138.41, 139.60, 169.99, 170.05, 173.13
Anal. calcd for C$_{42}$H$_{38}$O$_6$N$_2$: C, 75.66; H, 5.74; N, 4.20. Found: C, 75.71; H, 5.85; N, 4.18.

EXAMPLE 5

Synthesis of (S)-6-(2-methoxycarbonyl)ethyl-2,2'-diamido-(N,N'-bis((S)-1-amino-1-tert-butyl-2-hydroxy-ethane)-1,1'-binaphthyl((S,S)-tb-amidoalcohol: a Compound of the General Formula (3))

The same procedure of Example 3 was carried out except that (S)-tert-leucinol was used instead of (S)valinol. The title compound was obtained as a white solid with a yield of 70%.

Its physical property values are as follows.
$[\alpha]^2_D$ −99.60 (C=0.55, THF)
$^1$H-NMR (CDCl$_3$) δ (ppm) 0.65 (s, 9H), 0.67 (s, 9H), 1.67 (s, br, 2H), 2.68 (t, J=7.9, 1H), 3.07 8t, J=7.9 Hz, 2H), 3.15 (m, 2H), 3.53 (m, 2H), 3.66 (s, 3H), 3.67 (m, 2H), 7.02 (d, J=9.8 Hz, 1H), 7.10 (d, J=9.8 Hz, 1H), 7.19 (s, 2H), 7.25 (d, J=8.2 Hz, 1H), 7.33 (td, J$_1$=7.7 Hz, J$_2$=1.2 Hz, 1H), 7.49 (td, J$_1$=7.6 Hz, J$_2$=1.2 Hz, 1H), 7.67 (m, 2H), 7.72 (s, 1H), 7.92 (d, J=8.3 Hz, 1H), 7.94 (d, J=8.6 Hz, 1H), 8.01 (d, J=8.3 Hz, 1H)
$^{13}$C-NMR (CDCl$_3$) δ (ppm) 26.46, 26.49, 30.80, 33.31, 33.38, 35.20, 51.66, 59.38, 59.48, 62.30, 62.38, 123.75, 123.98, 126.72, 126.80, 127.07, 127.14, 127.41, 128.15, 128.48, 128.54, 128.92, 131.48, 132.70, 132.83, 132.92, 133.69, 133.92, 135.00, 135.48, 139.46, 171.26, 171.36, 173.13
Anal. calcd for C$_{38}$H$_{46}$O$_6$N$_2$: C, 72.82; H, 7.40; N, 4.47. Found: C, 73.03; H, 7.31; N, 4.31.

EXAMPLE 6

Synthesis of (S)-6-(2-methoxycarbonyl)ethyl-2,2'-diamido-(N,N'-bis(1-amino-1,1-dimethyl-2-hydroxy-ethane)-1,1'-binaphthyl((S)-dm-amidoalcohol: a Compound of the General Formula (3))

The same procedure of Example 3 was carried out except that 2-amino-2-methyl-1-propanol was used instead of (S)-valinol. The title compound was obtained as a white solid with a yield of 89%.

Its physical property values are as follows.
$[\alpha]^{25}_D$ −168.80 (C=0.56, THF)
$^1$H-NMR (CDCl$_3$) δ (ppm) 0.57 (s, 3H), 0.64 (s, 3H), 0.74 (s, 3H), 0.81 (s, 3H), 2.69 (t, J=8.8, 2H), 3.08–3.19 (m, 6H), 3.65 (s, 3H), 3.98 (s, br, 2H), 6.71 (s, 1H), 6.83 (s, 1H), 7.15–7.27 (m, 4H), 7.74 (s, 1H), 7.95 (d, J=8.5 Hz, 1H), 7.97 (d, J=8.6 Hz, 1H), 8.01 (d, J=8.6 Hz, 1H)
$^{13}$C-NMR (CDCl$_3$) δ (ppm) 22.66, 23.10, 23.60, 23.71, 30.85, 35.27, 51.73, 56.11, 69.90, 69.93, 123.79, 124.26, 126.34, 126.69, 126.85, 127.25, 127.47, 128.29, 128.57, 128.63, 129.03, 131.00, 132.16, 132.23, 132.53, 133.90, 134.19, 134.79, 135.28, 139.59, 170.51, 170.66, 173.26
Anal. calcd for C$_{34}$H$_{40}$O$_6$N$_2$: C, 72.31; H, 7.04; N, 4.89. Found: C, 71.10; H, 7.03; N, 4.85.

EXAMPLE 7

Synthesis of (S)-6-(2-methoxycarbonyl)ethyl-2,2'-bis((S)-4-isopropyloxazolin-2-yl)-1,1'-binaphthyl((S,S)-ip-boxax Methyl Ester: a Compound of the General Formula (2))

At 0° C., 1.1 equivalents of methanesulfonyl chloride was added to a solution prepared by dissolving 1 equivalent of (S)-6-(2-methoxycarbonyl)ethyl-2,2'-diamido-(N,N'-bis ((S)-1-amino-1-isopropyl-2-hydroxy-ethane)-1,1'-binaphthyl((S,S)-ip-amidoalcohol) obtained in Example 3 and 1.5 equivalents of diisopropylethylamine in methylene chloride, and the reaction mixture was then stirred overnight at 25° C. The reaction mixture was diluted with chloroform and washed with 1 N hydrochloric acid aqueous solution, saturated NaHCO$_3$ aqueous solution and saturated brine. The organic layer was dried with magnesium sulfate, and the solvent was evaporated under a reduced pressure. The resulting residue was purified by a silica gel column chromatography. The title compound was obtained as a white solid with a yield of 82%.

Its physical property values are as follows.
$[\alpha]^{25}_D$ −97.75 (C=0.75, THF)
$^1$H-NMR (CDCl$_3$) δ (ppm) 0.58 (m, 12H), 1.30 (m, 2H), 2.68 (t, J=7.8, 2H), 3.07 (t, J=7.8 Hz, 2H), 3.56–3.75 (m, 6H), 3.65 (s, 3H), 7.05 (dd, J$_1$=8.6 Hz, J$_2$=1.5 Hz, 1H), 7.11 (d, J=8.8 Hz, 1H), 7.17–7.23 (m, 2H), 7.45 (td, J$_1$=7.3 Hz, J$_2$=1.5 Hz, 1H), 7.68 (m, 1H), 7.86 (d, J=8.6 Hz, 1H), 7.88 (d, J=8.6 Hz, 1H), 7.93 (d, J=8.6 Hz, 1H), 8.08 (d, J=8.6 Hz, 1H), 8.09 (d, J=8.6 Hz, 1H)
$^{13}$C-NMR (CDCl$_3$) δ (ppm) 18.09, 18.11, 18.47, 18.50, 30.87, 32.62, 32.66, 35.32, 51.74, 69.97, 72.39, 125.39, 125.75, 126.13, 126.24, 126.30, 126.39, 126.69, 127.09, 127.12, 127.28, 127.41, 127.46, 127.69, 131.75, 132.97, 134.20, 134.42, 137.76, 137.97, 138.99, 163.75, 173.22
Anal. calcd for C$_{36}$H$_{38}$O$_4$N$_2$: C, 76.84; H, 6.81; N, 4.98. Found: C, 76.65; H, 6.78; N, 4.88.

EXAMPLE 8

Synthesis of (S)-6-(2-methoxycarbonyl)ethyl-2,2'-bis((S)-4-phenyloxazolin-2-yl)-1,1'-binaphthyl((S,S)-ph-boxax Methyl Ester: a Compound of the General Formula (2))

The same procedure of Example 7 was carried out except that the (S,S)-ph-amidoalcohol obtained in Example 4 was used instead of the (S,S)-ip-amidoalcohol. The title compound was obtained as a white solid with a yield of 95%.

Its physical property values are as follows.
[α]$^{25}_D$ −16.93 (C=0.48, THF)
$^1$H-NMR (CDCl$_3$) δ (ppm) 2.71 (t, J=7.8 Hz, 2H), 3.11 (t, J=7.8 Hz, 2H), 3.67 (s, 3H), 3.73 (m 2H), 4.20 (m, 2H), 5.05 (m, 2H), 6.68–6.73 (m, 4H), 7.05–7.30 (m, 10H), 7.52 (td, J$_1$=7.4 Hz, J$_2$=1.2 Hz, 1H), 7.74 (m, 1H), 7.90 (d, J=8.8 Hz, 1H), 8.16 (d, J=8.8 Hz, 1H), 8.18 (d, J=8.6 Hz, 1H)
$^{13}$C-NMR (CDCl$_3$) δ (ppm) 30.94, 35.27, 51.71, 69.77, 74.43, 74.47, 125.15, 125.54, 126.16, 126.29, 126.32, 126.37, 126.41, 126.50, 126.88, 126.93, 127.06, 127.25, 127.35, 127.55, 127.62, 127.82, 128.19, 128.20, 131.68, 132.92, 134.35, 134.56, 137.83, 138.03, 139.23, 142.37, 142.39, 165.05, 165.10, 173.09
Anal. calcd for C$_{42}$H$_{34}$O$_4$N$_2$: C, 79.98; H, 5.43; N, 4.44. Found: C, 80.05; H, 5.38; N, 4.41.

EXAMPLE 9

Synthesis of (S)-6-(2-methoxycarbonyl)ethyl-2,2'-bis((S)-4-tert-butyloxazolin-2-yl)-1,1'-binaphthyl((S,S)-tp-boxax Methyl Ester: a Compound of the General Formula (2))

The same procedure of Example 7 was carried out except that the (S,S)-tb-amidoalcohol obtained in Example 5 was used instead of the (S,S)-ip-amidoalcohol. The title compound was obtained as a white solid with a yield of 79%.
Its physical property values are as follows.
[α]$^{25}_D$ −54.95 (C=0.58, THF)
$^1$H-NMR (CDCl$_3$) δ (ppm) 2.66 (t, J=8.0 Hz, 2H), 3.00 (t, J=8.0 Hz, 2H), 3.66 (s, 3H), 3.67 (m, 6H), 7.03 (dd, J$_1$=8.8 Hz, J$_2$=1.7 Hz, 1H), 7.07 (d, J=8.8 Hz, 1H) 7.14 (d, J=8.6 Hz, 1H), 7.18 (td, J$_1$=7.6 Hz, J$_2$=1.2 Hz, 1H), 7.43 (td, J$_1$=7.4 Hz, J$_2$=1.4 Hz, 1H), 7.67 (d, J=1.2 Hz, 1H), 7.85 (d, J=8.8 Hz, 1H), 7.88 (d, J=8.3 Hz, 1H), 7.92 (d, J=8.8 Hz, 1H), 8.10 (d, J=8.6 Hz, 1H), 8.11 (d, J=8.6 Hz, 1H)
$^{13}$C-NMR (CDCl$_3$) δ (ppm) 25.47, 30.95, 33.56, 35.44, 51.67, 68.06, 76.01, 76.04, 125.08, 125.42, 125.98, 126.11, 126.19, 126.25, 126.58, 126.88, 127.10, 127.15, 127.25, 127.39, 127.56, 131.75, 132.97, 134.17, 134.40, 138.06, 138.28, 138.87, 163.01, 163.06, 173.10
Anal. calcd for C$_{38}$H$_{42}$O$_4$N$_2$: C, 77.26; H, 7.17; N, 4.74. Found: C, 77.09; H, 7.25; N, 4.67.

EXAMPLE 10

Synthesis of (S)-6-(2-methoxycarbonyl)ethyl-2,2'-bis(4,4'-dimethyl-oxazolin-2-yl)-1,1'-binaphthyl((S)-dm-boxax Methyl Ester: a Compound of the General Formula (2))

The same procedure of Example 7 was carried out except that the (S,S)-dm-amidoalcohol obtained in Example 6 was used instead of the (S,S)-ip-amidoalcohol. The title compound was obtained as a white solid with a yield of 82%.
Its physical property values are as follows.
[α]$^{25}_D$ −7.28 (C=0.49, THF)
$^1$H-NMR (CDCl$_3$) δ (ppm) 0.94 (s, 3H), 0.96 (s, 3H), 1.11 (s, 3H), 1.12 (s, 3H), 2.69 (t, J=7.8 Hz, 2H), 3.08 (t, J=7.8 Hz, 2H), 3.24 (m, 2H), 3.50 (m, 2H), 3.66 (s, 3H), 7.12 (dd, J$_1$=8.8 Hz, J$_2$=1.5 Hz, 1H), 7.20 (d, J=8.8 Hz, 1H), 7.27 (d, J=8.6 Hz, 1H), 7.48 (m, 1H), 7.70 (m, 1H), 7.87 (d, J=8.6 Hz, 1H), 7.91 (d, J=7.8 Hz, 1H), 7.94 (d, J=8.6 Hz, 1H), 7.98 (m, 2H)
$^{13}$C-NMR (CDCl$_3$) δ (ppm) 27.97, 28.00, 30.99, 35.38, 51.76, 66.92, 79.38, 79.41, 126.00, 126.34, 126.41, 126.54, 126.62, 126.85, 127.46, 127.58, 127.76, 127.84, 127.94, 131.71, 132.95, 134.14, 134.36, 137.01, 137.24, 139.17, 163.70, 173.33
Anal. calcd for C$_{34}$H$_{36}$O$_4$N$_2$: C, 76.09; H, 6.76; N, 5.22. Found: C, 76.15; H, 6.82; N, 5.05.

EXAMPLE 11

Synthesis of Polystyrene-Polyethylene Glycol-(S)-6-(2-methoxycarbonyl)ethyl-2,2'-bis((S)-4-isopropyloxazolin-2-yl)-1,1'-binaphthyl((PS-PEG-(S,S)-ip-boxax: a Compound of the General Formula (1))

A solution prepared from 1 equivalent of the (S)-6-(2-methoxycarbonyl)ethyl-2,2'-bis((S)-4-isopropyloxazolin 2-yl)-1,1'-binaphthyl((S,S)-ip-boxax methyl ester) obtained in Example 7, 1.05 equivalents of lithium hydroxide monohydrate and a tetrahydrofuran/water mixed solution was stirred at 25° C. for 24 hours. By concentrating the reaction mixture under a reduced pressure, a lithium carboxylate was obtained as a white precipitate. This was put into a Merrifield Vessel together with 1 equivalent of ArgoGel-NH$_2$ (mfd. by Argonaut Technologies, amino group content 0.37 mmol/g), 2.5 equivalents of 1-(3-dimethylaminopropyl)-3-ethylcarbodiimide (EDCl) and 1.0 equivalent of N-hydroxybenzotriazole (HOBt), suspended by adding N,N-dimethylformamide and then shaken at 25° C. for 12 hours. This was further mixed with 5.0 equivalents of 1-(3-dimethylaminopropyl)-3-ethylcarbodiimide (EDCl) and shaken at 25° C. for 24 hours. The mixture was filtered, and the thus obtained resin was washed with N,N-dimethylformamide, methanol and methylene chloride. By drying the thus obtained immobilized carrier under a reduced pressure, the polymer-carrying optically active binaphthyl type oxazoline compound was obtained.
Its physical property values are as follows.
$^{13}$C-MASNMR δ (ppm) 17.92, 18.25, 31.35, 35.26, 32.36, 37.33, 39.01, 69.64, 72.08, 124.86, 125.39, 131.29, 132.62, 133.79, 134.04, 134.12, 137.63, 139.31, 163.31, 171.63

EXAMPLE 12

Synthesis of Polystyrene-Polyethylene Glycol-(S)-6-(2-methoxycarbonyl)ethyl-2,2'-bis((S)-4-phenyloxazolin-2-yl)-1,1'-binaphthyl((PS-PEG-(S,S)-ph-boxax: a Compound of the General Formula (1))

The title compound was obtained by carrying out the same procedure of Example 11 except that the (S,S)-ph-amidoalcohol obtained in Example 8 was used instead of the (S,S)-ip-amidoalcohol.
Its physical property values are as follows.
$^{13}$C-MASNMR δ (ppm) 31.26, 37.12, 38.94, 74.10, 131.23, 132.58, 133.97, 134.27, 137.46, 137.81, 139.70, 142.05, 164.68, 171.68

EXAMPLE 13

Synthesis of Polystyrene-Polyethylene Glycol-(S)-6-(2-methoxycarbonyl)ethyl-2,2'-bis((S)-4-tert-butyloxazolin-2-yl)-1,1'-binaphthyl((PS-PEG-(S,S)-tb-boxax: a Compound of the General Formula (1))

The title compound was obtained by carrying out the same procedure of Example 11 except that the (S,S)-tb-amidoalcohol obtained in Example 9 was used instead of the (S,S)-ip-amidoalcohol.

Its physical property values are as follows.
$^{13}$C-MASNMR δ (ppm) 26.67, 31.30, 37.29, 39.00, 66.53, 78.96, 125.40, 131.17, 132.50, 133.60, 133.88, 136.54, 139.35, 163.06, 171.59

EXAMPLE 14

Synthesis of Polystyrene-Polyethylene Glycol-(S)-6-(2-methoxycarbonyl)ethyl-2,2'-bis(4,4'-dimethyl-oxazolin-2-yl)-1,1'-binaphthyl((PS-PEG-(S)-dm-boxax: a Compound of the General Formula (1))

The title compound was obtained by carrying out the same procedure of Example 11 except that the (S)-dm-amidoalcohol obtained in Example 10 was used instead of the (S,S)-ip-amidoalcohol.

Its physical property values are as follows.
$^{13}$C-MASNMR δ (ppm) 27.67, 31.30, 37.29, 39.00, 66.53, 78.96, 125.40, 131.17, 132.50, 133.60, 133.88, 136.54, 136.82, 139.35, 163.06, 171.59

EXAMPLE 15

Synthesis of Polystyrene-(S)-6-(2-methoxycarbonyl) ethyl-2,2'-bis((S)-4-phenyloxazolin-2-yl)-1,1'-binaphthyl((PS-(S,S)-ph-boxax: a Compound of the General Formula (1))

The title compound was obtained by carrying out the same procedure of Example 11, except that aminomethylated polystyrene was used instead of the ArgoGel-NH$_2$ (mfd. by Argonaut Technologies, amino group content 0.37 mmol/g), and the (S,S)-ph-amidoalcohol obtained in Example 8 was used instead of the (S,S)-ip-amidoalcohol.

Its physical property values are as follows.
$^{13}$C-MASNMR δ (ppm) 31.52, 37.52, 74.23, 131.55, 132.82, 134.24, 134.45, 137.80, 137.99, 139.75, 142.24, 164.85, 171.37

EXAMPLE 16

Synthesis of Acrylamidopropyl[2-aminopropyl]poly (ethylene Glycol)-N,N-dimethylacrylamido-(S)-6-(2-methoxycarbonyl)ethyl-2,2'-bis((S)-4-phenyloxazolin-2-yl)-1,1'-binaphthyl((PEGA-(S,S)-ph-boxax: a Compound of the General Formula (1))

The title compound was obtained by carrying out the same procedure of Example 11, except that a copolymer of acrylamidopropyl[2-aminopropyl]poly(ethylene glycol) and N,N-dimethylacrylamide was used instead of the ArgoGel-NH$_2$ (mfd. by Argonaut Technologies, amino group content 0.37 mmol/g), and the (S,S)-ph-amidoalcohol obtained in Example 8 was used instead of the (S,S)-ip-amidoalcohol.

Its physical property values are as follows.
$^{13}$C-MASNMR δ (ppm) 31.77, 131.69, 133.03, 134.41, 134.62, 137.91, 138.16, 139.98, 142.48, 165.10, 171.23

EXAMPLE 17

Synthesis of Methoxypolyethylene Glycol-(S)-6-(2-methoxycarbonyl)ethyl-2,2'-bis((S)-4-phenyloxazolin-2-yl)-1,1'-binaphthyl((MeO-PEG-(S,S)-ph-boxax: a Compound of the General Formula (1))

A solution composed of 1.1 equivalents of (S)-6-(2-methoxycarbonyl)ethyl-2,2'-bis((S)-4-phenyloxazolin-2-yl)-1,1'-binaphthyl (26 b), 1.15 equivalents of lithium hydroxide monohydrate and a tetrahydrofuran/water mixed solution was stirred at 25° C. for 24 hours. By concentrating the reaction mixture under a reduced pressure, a lithium carboxylate was obtained as a white precipitate. This was put into a Merrifield Vessel together with 1.0 equivalent of MeO-PEG$_{5000}$-NH$_2$ (mfd. by Fluka, amino group content 0.17 mmol/g), 2.5 equivalents of 1-(3-dimethylaminopropyl)-3-ethylcarbodiimide (EDCl) and 2.5 equivalents of N-hydroxybenzotriazole (HOBt), suspended by adding 20 ml of acetonitrile and then shaken at room temperature for 18 hours. This was further mixed with 5.0 equivalents of 1-(3-dimethylaminopropyl)-3-ethylcarbodiimide (EDCl) and shaken at room temperature for 24 hours. Excess amount of acetyl chloride/triethylamine was added to the mixture. By removing the solvent and then recrystallizing the crude product from methanol, the title compound was obtained as light yellow solid with a yield of 85%.

Its physical property values are as follows.
$^{1}$H-NMR (CDCl$_3$) δ (ppm) 2.56 (t, J=7.8 Hz, 2H), 3.13 (t, J=7.8H, 2H), 4.21 (m, 2H), 5.05 (m, 2H), 6.01 (t, J=7.0 Hz, 1H), 6.68–6.73 (m, 4H), 7.07–7.30 (m, 10H), 7.52 (td, J$_1$=7.4 Hz, J$_2$=1.2 Hz, 1H), 7.76 (s, 1H), 7.90 (d, J=8.8 Hz, 1H), 7.94 (d, J=8.0 Hz, 1H), 7.96 (d, J=8.8 Hz, 1H), 8.16 (d, J=8.8 Hz, 1H), 8.18 (d, J=8.8 Hz, 1H)

$^{13}$C-NMR (CDCl$_3$) δ (ppm) 31.61, 37.72, 39.29, 59.03, 125.53, 126.27, 126.31, 126.44, 126.91, 127.22, 127.68, 127.82, 128.19, 131.61, 134.33, 134.57, 138.07, 139.84, 142.38, 165.05

EXAMPLE 18

Preparation of Palladium Complex of PS-PEG-(S,S)-ip-boxax

One equivalent of tetrakis(acetonitrile)palladium(II) bis (tetrafluoroborate) was added to and dissolved in acetonitrile, 1 equivalent of the PS-PEG-(S,S)-ip-boxax obtained as a polymer-carrying optically active binaphthyl type oxazoline compound in Example 11 was added thereto, and the mixture was stirred at 25° C. for 1 hour. This was filtered and dried under a reduced pressure to obtain the title compound as a yellow solid.

EXAMPLE 19

Preparation of Palladium Complex of PS-PEG-(S,S)-ph-boxax

The title compound was obtained as a yellow solid by carrying out the same procedure of Example 18, except that the PS-PEG-(S,S)-ip-boxax obtained in Example 12 was used instead of the PS-PEG-(S,S)-ip-boxax.

EXAMPLE 20

Preparation of Palladium Complex of PS-PEG-(S,S)-tb-boxax

The title compound was obtained as a yellow solid by carrying out the same procedure of Example 18, except that the PS-PEG-(S,S)-tb-boxax obtained in Example 13 was used instead of the PS-PEG-(S,S)-ip-boxax.

EXAMPLE 21

Preparation of Palladium Complex of PS-PEG-(S)-dm-boxax

The title compound was obtained as a yellow solid by carrying out the same procedure of Example 18, except that the PS-PEG-(S)-dm-boxax obtained in Example 14 was used instead of the PS-PEG-(S,S)-ip-boxax.

EXAMPLE 22

Preparation of Palladium Complex of PS-(S,S)-ph-boxax

The title compound was obtained as a yellow solid by carrying out the same procedure of Example 18, except that the PS-(S,S)-ph-boxax obtained in Example 15 was used instead of the PS-PEG-(S,S)-ip-boxax.

EXAMPLE 23

Preparation of Palladium Complex of PEGA-(S,S)-ph-boxax

The title compound was obtained as a yellow solid by carrying out the same procedure of Example 18, except that the PEGA-(S,S)-ph-boxax obtained in Example 16 was used instead of the PS-PEG-(S,S)-ip-boxax.

EXAMPLE 24

Preparation of Palladium Complex of MeO-PEG-(S,S)-ph-boxax

The title compound was obtained as a yellow solid by carrying out the same procedure of Example 18, except that the MeO-PEG-(S,S)-ph-boxax obtained in Example 17 was used instead of the PS-PEG-(S,S)-ip-boxax.

EXAMPLES 25 TO 29 AND REFERENCE EXAMPLES 1 AND 2

Wacker Type Asymmetric Cyclization Reaction of o-allylphenol

A polymer-carrying optically active binaphthyl type oxazoline compound-palladium complex (palladium content, 0.02 mmol), 35.2 mg (0.2 mmol) of 2-(2,3-dimethyl-2-butenyl)-phenol and 86.4 mg (0.8 mmol) of benzoquinone were added to 1 ml of methanol and then stirred at 60° C. for 20 hours. After cooling to room temperature, the resin was filtered and washed twice with 1 ml of methanol. The solution was concentrated under a reduced pressure, and the resulting residue was purified by a silica gel column chromatography (hexane/ethyl acetate=95/5) to obtain (S)-2-isopropenyl-2-methyl-2,3-dihydrobenzofuran as a colorless oil.

Its optical purity was determined by carrying out a gas chromatography analysis using a column for optically active substance separation use (Cyclodexβ236M).

Similar reactions were carried out as Reference Example 1 using (S,S)-ip-boxax, and as Reference Example 2 using one of the compounds of general formula (2) of the invention, ((S,S)-ip-boxax methyl ester) synthesized in Example 7.

In this connection, when MeO-PEG-(S,S)-ph-boxax was used as the ligand of Example 29, the reaction was carried out in the same manner by using a palladium complex prepared by allowing the ligand to react with a palladium compound, without isolating it from the reaction system.

The results are shown in Table 1.

TABLE 1

| | Ligand | Conversion (%) | Optical. purity (% ee) |
|---|---|---|---|
| Example 25 | PS-PEG-(S,S)-ip-boxax | 38 | 91 (S) |
| Example 26 | PS-PEG-(S,S)-ph-boxax | 17 | 91 (S) |
| Example 27 | PS-(S,S)-ph-boxax | 15 | 84 (S) |
| Example 28 | PEGA-(S,S)-ph-boxax | 27 | 96 (S) |
| Example 29 | MeO-PEG-(S,S)-ph-boxax | 47 | 95 (S) |
| Ref. Ex. 1 | (S,S)-ip-boxax | 99 | 85 (S) |
| Ref. Ex. 2 | (S,S)-ip-boxax (Me Ester) | 62 | 94 (S) |

As is evident also from Table 1, the polymer-carrying optically active binaphthyl type oxazoline compound-palladium complex of the invention was markedly excellent in obtaining the compound of interest with a high optical purity of 84% or more in both of the case in which the palladium complex was used by preparing it in advance (Examples 25 to 28) and the case in which it was used by preparing it in the reaction system (Example 29).

Also, though the conversion ratio in Examples 25 to 29 was within the range of from 15 to 47% which seemed to be inferior to the conversion ratio of 99% in Reference Example 1, it was confirmed that the reaction completes almost quantitatively when a catalyst which uses the polymer-carrying optically active binaphthyl type oxazoline compound of the invention is recovered and recycled.

Accordingly, since the ligand can be recycled, the catalyst of the invention is superior to the conventional homogeneous catalysts from the viewpoint of cost and environmental sides.

It was confirmed also that, when the reaction is carried out using the (S,S)-ip-boxax methyl ester obtained in Example 7 as the ligand which is a precursor of the polymer-carrying optically active binaphthyl type oxazoline compound of the invention, the compound of interest can be obtained with a conversion ratio of 62% and an optical purity of 94% ee so that the catalyst can be used in almost the same manner as the case of the conventional homogenous catalysts.

According to the invention, there is provided a polymer-carrying optically active binaphthyl type oxazoline compound which, after completion of the asymmetric synthesis reaction, does not require complex steps for the recovery of the catalyst that uses an optically active binaphthyl type oxazoline compound as the ligand, and it also provides a polymer-carrying optically active binaphthyl type oxazoline compound which is useful as a ligand capable of achieving high asymmetric yield in various asymmetric synthesis reactions that use a transition metal complex catalyst, such as Wacker type asymmetric cyclization reaction of olefin compounds.

While the invention has been described in detail and with reference to specific embodiments thereof, it will be apparent to one skilled in the art that various changes and modifications can be made therein without departing from the scope thereof.

This application is based on Japanese patent application No. 2002-332398 filed Nov. 15, 2002, the entire contents thereof being hereby incorporated by reference.

What is claimed is:

1. A polymer-carrying optically active binaphthyl oxazoline compound having axial asymmetry, represented by formula (1):

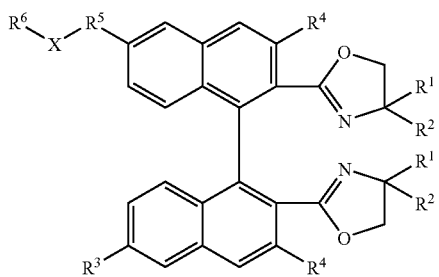

wherein:
- $R^1$ and $R^2$ independently represent a hydrogen atom, an alkyl group having from 1 to 6 carbon atoms, or an aryl group which may have a substituent or a benzyl group which may have a substituent;
- $R^3$ represents a hydrogen atom or $-R^5-X-R^6$;
- $R^4$ represents a hydrogen atom, an alkyl group having from 1 to 4 carbon atoms or a tri($C_{1-4}$ alkyl)silyl group;
- $R^5$ represents a straight- or branched-chain aliphatic hydrocarbon chain which may have a directly or indirectly bonded substituent;
- X represents $CH_2$, $CO_2$, O, $CONR^7$ or $NR^7$;
- $R^6$ represents a directly or indirectly bonded polymer; and
- $R^7$ represents a hydrogen atom or an alkyl group having from 1 to 4 carbon atoms.

2. The oxazoline derivative according to claim 1, wherein the polymer is one or more species selected from polyamides, polystyrenes, polyethers and polyethylenes.

3. A transition metal complex which contains the oxazoline derivative of claim 1 or 2 as the ligand.

4. The transition metal complex according to claim 3, wherein the transition metal is at least one transition metal selected from palladium, iridium, rhodium, ruthenium, nickel, copper and platinum.

5. An optically active binaphthyl oxazoline compound having axial asymmetry, represented by formula (2):

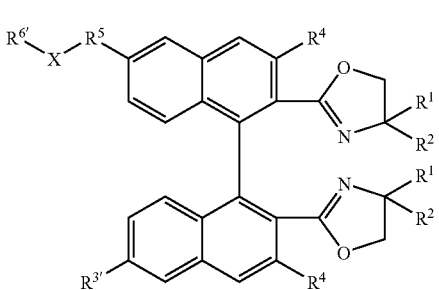

wherein $R^1$ and $R^2$ independently represent a hydrogen atom, an alkyl group having from 1 to 6 carbon atoms, or an aryl group which may have a substituent or a benzyl group which may have a substituent;
- $R^{3'}$ represents a hydrogen atom or $-R^5-X-R^{6'}$;
- $R^4$ represents a hydrogen atom, an alkyl group having from 1 to 4 carbon atoms or a tri($C_{1-4}$ alkyl)silyl group;
- $R^5$ represents a straight- or branched-chain aliphatic hydrocarbon chain which may have a directly or indirectly bonded substituent;
- X represents $CH_2$, $CO_2$, O, $CONR^7$ or $NR^7$; and
- $R^{6'}$ represents a hydrogen atom or an alkyl group having from 1 to 6 carbon atoms.

* * * * *

UNITED STATES PATENT AND TRADEMARK OFFICE
CERTIFICATE OF CORRECTION

PATENT NO. : 7,164,026 B2
APPLICATION NO. : 10/704576
DATED : January 16, 2007
INVENTOR(S) : Yasuhiro Uozumi et al.

It is certified that error appears in the above-identified patent and that said Letters Patent is hereby corrected as shown below:

ON TITLE PAGE AT (75) INVENTORS

"Kenyo Sumi, Ohtu-ku (JP)" should read --Kenyo Sumi, Tokyo (JP)--.

ON TITLE PAGE AT (56) OTHER PUBLICATIONS

After "Cai": "Lett rs," should read --Letters,--.

ON TITLE PAGE AT (57) ABSTRACT

Line 12, "to" should be deleted.

COLUMN 1

Line 35, "have" should read --has--.

COLUMN 2

Line 4, "separation" should read --separated--.

COLUMN 8

Line 41, "$R^3$," should read --$R^{3'}$,--.

COLUMN 14

Line 63, "or 13," should read --or $I_3$,--.

COLUMN 16

Line 2, "(cod) 2]BF$_4$)" should read --(cod)$_2$]BF$_4$)--.

COLUMN 17

Line 3, "NiCl$_2$(L), NiBr$_2$ (L), NiI$_2$(L)" should read --NiCl$_2$(L), NiBr$_2$(L), NiI$_2$(L)--; and
Line 15, "Cu$_4$F$_4$(L) 2, Cu$_4$Cl$_4$(L) 2, Cu$_4$Br$_4$(L) 2, Cu$_4$I$_4$(L)$_2$, Cu$_4$H$_4$(L)$_2$," should read
--Cu$_4$F$_4$(L)$_2$, CU$_4$Cl$_4$(L)$_2$, Cu$_4$Br$_4$(L)$_2$, Cu$_4$I$_4$(L)$_2$, Cu$_4$H$_4$(L)$_2$,--.

COLUMN 21

Line 26, "$[\alpha]^2_D$+6.22 (C=0.52, THF)" should read --$[\alpha]^{25}_D$+6.22 (C=0.52, THF)--.

UNITED STATES PATENT AND TRADEMARK OFFICE
CERTIFICATE OF CORRECTION

PATENT NO. : 7,164,026 B2
APPLICATION NO. : 10/704576
DATED : January 16, 2007
INVENTOR(S) : Yasuhiro Uozumi et al.

It is certified that error appears in the above-identified patent and that said Letters Patent is hereby corrected as shown below:

COLUMN 24

Line 61, "of" should be deleted--.

COLUMN 25

Line 16, "binaphthyl as" should read --binaphthyl was obtained as--.

COLUMN 26

Line 17, "trifluotomethanesulfonic" should read --trifluoromethanesulfonic--.

COLUMN 29

Line 39, "$[\alpha]^2_D$-99.60 (C=0.55, THF)" should read --$[\alpha]^{25}_D$-99.60 (C=0.55, THF)--.

Signed and Sealed this

Twenty-second Day of May, 2007

JON W. DUDAS
*Director of the United States Patent and Trademark Office*